US 8,501,934 B2
Aug. 6, 2013

(12) United States Patent
Howard et al.

(10) Patent No.: US 8,501,934 B2
(45) Date of Patent: Aug. 6, 2013

(54) PYRROLOBENZODIAZEPINES

(75) Inventors: Philip Wilson Howard, London (GB);
Stephen John Gregson, London (GB);
Zhizhi Chen, London (GB); Arnaud Charles Tiberghien, London (GB);
Luke Masterson, London (GB)

(73) Assignee: Spirogen SARL, St-Legier-La Chiesaz (CH)

( * ) Notice: Subject to any disclaimer, the term of this patent is extended or adjusted under 35 U.S.C. 154(b) by 305 days.

(21) Appl. No.: 13/055,194

(22) PCT Filed: Jul. 22, 2009

(86) PCT No.: PCT/GB2009/001819
§ 371 (c)(1),
(2), (4) Date: Mar. 18, 2011

(87) PCT Pub. No.: WO2010/010347
PCT Pub. Date: Jan. 28, 2010

(65) Prior Publication Data
US 2011/0162227 A1    Jul. 7, 2011

(30) Foreign Application Priority Data
Jul. 22, 2008 (GB) .................................. 0813432.2

(51) Int. Cl.
A61P 35/00 (2006.01)
A61K 31/5517 (2006.01)
C07D 487/04 (2006.01)

(52) U.S. Cl.
USPC ........................................................ 540/496

(58) Field of Classification Search
USPC ........................................................ 540/496
See application file for complete search history.

(56) References Cited

U.S. PATENT DOCUMENTS

| | | | |
|---|---|---|---|
| 4,309,437 A | 1/1982 | Ueda et al. |
| 5,418,241 A | 5/1995 | Jegham et al. |
| 6,187,797 B1 | 2/2001 | Pruitt et al. |
| 6,562,806 B1 | 5/2003 | Thurston et al. |
| 6,608,192 B1 | 8/2003 | Thurston et al. |
| 6,660,856 B2 | 12/2003 | Wang |
| 6,747,144 B1 | 6/2004 | Thurston et al. |
| 6,909,006 B1 | 6/2005 | Thurston et al. |
| 7,049,311 B1 | 5/2006 | Thurston et al. |
| 7,067,511 B2 | 6/2006 | Thurston et al. |
| 7,265,105 B2 | 9/2007 | Thurston et al. |
| 7,407,951 B2 | 8/2008 | Thurston et al. |
| 7,429,658 B2 | 9/2008 | Howard et al. |
| 7,528,126 B2 | 5/2009 | Howard et al. |
| 7,557,099 B2 | 7/2009 | Howard et al. |
| 7,612,062 B2 | 11/2009 | Howard et al. |
| 7,704,924 B2 | 4/2010 | Thurston et al. |
| 7,741,319 B2 | 6/2010 | Howard et al. |
| 2003/0195196 A1 | 10/2003 | Thurston et al. |
| 2004/0138269 A1 | 7/2004 | Sun et al. |
| 2004/0198722 A1 | 10/2004 | Thurston et al. |
| 2007/0072846 A1 | 3/2007 | Vishnuvajjala et al. |
| 2007/0191349 A1 | 8/2007 | Howard et al. |
| 2007/0249591 A1 | 10/2007 | Howard et al. |
| 2008/0090812 A1 | 4/2008 | Pepper et al. |
| 2008/0214525 A1 | 9/2008 | Howard et al. |
| 2010/0113425 A1 | 5/2010 | Howard et al. |
| 2011/0160192 A1 | 6/2011 | Howard et al. |

FOREIGN PATENT DOCUMENTS

| | | |
|---|---|---|
| EP | 1193270 | 4/2002 |
| FR | 2586683 | 3/1987 |
| GB | 2053894 | 2/1981 |
| JP | 55069587 | 5/1980 |
| JP | 58180487 | 10/1983 |
| WO | WO 93/18045 | 9/1993 |
| WO | WO 00/12506 | 3/2000 |
| WO | WO 00/12507 | 3/2000 |
| WO | WO 00/12508 | 3/2000 |
| WO | WO 00/12509 | 3/2000 |

(Continued)

OTHER PUBLICATIONS

United States Patent Office Action for U.S. Appl. No. 13/041,849 dated Jun. 6, 2012 (13 pages).

(Continued)

Primary Examiner — Brenda Coleman
(74) Attorney, Agent, or Firm — Michael Best & Friedrich LLP

(57) ABSTRACT

Methods of preparing ZC-423 (I) which result in varying enantiomeric ratios.

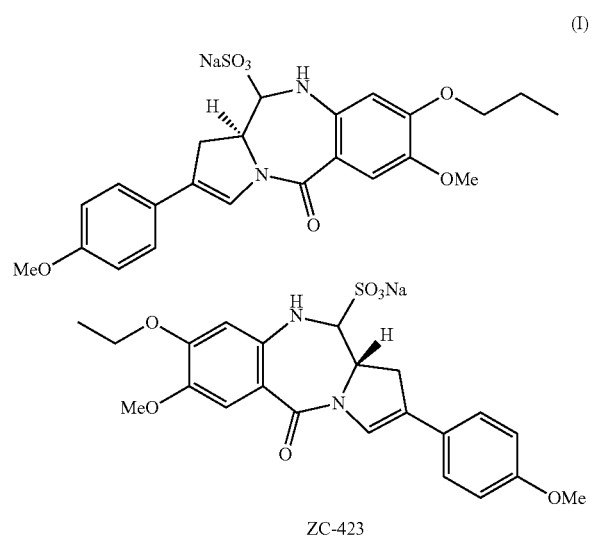

ZC-423

18 Claims, 2 Drawing Sheets

FOREIGN PATENT DOCUMENTS

| | | |
|---|---|---|
| WO | WO 2004/043963 | 5/2004 |
| WO | WO 2005/023814 | 3/2005 |
| WO | WO 2005/040170 | 5/2005 |
| WO | WO 2005/042535 | 5/2005 |
| WO | WO 2005/085250 | 9/2005 |
| WO | WO 2005/085251 | 9/2005 |
| WO | WO 2005/085259 | 9/2005 |
| WO | WO 2005/085260 | 9/2005 |
| WO | WO 2005/110423 | 11/2005 |
| WO | WO 2006/111759 | 10/2006 |
| WO | 2010/043880 | 4/2010 |

OTHER PUBLICATIONS

United States Patent Office Action for U.S. Appl. No. 13/041,849 dated Aug. 22, 2012 (8 pages).
Howard, P.W. et al., "Synthesis of a nvoel C2/C2'-aryl-substituted pyrrolo[2,1-c][1,4]benzodiazepine dimer prodrug with improved water solubility and reduced DNA reaction rate," Bioorg. Med. Chem. Lett. (2009) 19:6463-6466.
Althius, T. H. and Hess, H. J., "Synthesis and Identification of the Major Metabolites of Prazosin Formed in Dog and Rat," J. Medicinal Chem. (1977) 20(1):146-148.
Antonow, D. et al., "Parallel synthesis of a novel C2-aryl pyrrolo[2,1-c][1,4]benzodiazepine (PBD) library," J. Comb. Chem. (2007) 9:437-445.
Arima et al., "Studies on Tomaymycin, a New Antibiotic. I. Isolation and Properties of Tomaymycin," J. Antibiotics (1972) 25:437-444.
Berge et al., "Pharmaceutical Salts," J. Pharm. Sci. (1977) 66:1-19.
Bose et al., "New Approaches to Pyrrolo[2,1-c][1,4]benzodiazepines: Synthesis, DNA-binding and cytotoxicity of DC-81," Tetrahedron, 48, 751-758 (1992).
Dattolo, G. et al., "Polycondensed nitrogen heterocycles. IX. 5,6-dihydro-7H-pyrrolo[1,2-d][1,4]benzodiazepin-6-one," J. Heterocyclic. Chem. (1980) 17:701-703.
Dupont, C. et al., "Synthesis of rhazinilam analogue acting as an inhibitor of tubulin assembly," Tetrahedron Lett. (2000) 41:5853-5856.
Farmer, J.D. et al., "Synthesis and DNA crosslinking ability of a dimeric anthramycin analog," Tetrahedron Letters (1988) 29(40):5105-5108, Abstract only.
Fey, T. et al., "Silica-supported TEMPO catalysts: synthesis and application in the anelli oxidation of alcohols," J. Org. Chem. (2001) 66:8154-8159.
Firsching, A. et al., "Antiproliferative and angiostatic activity of suramin analogues," Cancer Res. (1995) 55:4957-4961.
Gregson, S. et al., "Synthesis of a novel C2/C2'-exo unsaturated pyrrolobenzodiazepine cross-linking agent with remarkable DNA binding affinity and cytotoxicity," Chemical Communications, 797-798 (1999).
Gregson, S.J. et al., "Linker length modulates DNA cross-linking reactivity and cytotoxic potency of C8/C8' ether-linked C2-exo-unsaturated pyrrolo[2,1-c][1,4]benzodiazepine (PBD) dimers," J. Med. Chem. (2004) 1161-1174.
Hara et al., "DC 102, a new glycosidic pyrrolo(1,4)benzodiazepine antibiotic produced by Streptomyces sp.", J. Antibiotics, 41, 702-704 (1988).
Hochlowski, J. et al., "Abbeymycin, a new anthramycin-type antibiotic produced by a streptomycete," J. Antibiotics, 40, 145-148 (1987).
Howard, P.W. et al., "Design, synthesis and biological evaluation of ZC-423, a novel C2-aryl substituted pyrrolobenzodiazepine (PBD) dimer," Clinical Cancer Research (2005) 11(23):9015S-9016S (A205).
Howard, P.W. et al., "The design, synthesis and biological evaluation of a set of C2-aryl substituted pyrrolo[2,1-c][1,4]benzodiazepine dimers," EJC Supplements (2006) 4(12):95—Poster Abstract 301.
Hu, W-P. et al., "An efficient synthesis of pyrrolo[2,1-c][1,4]benzodiazepine. Synthesis of the antibiotic DC-81," J. Org. Chem. (2001) 66:2881-2883.
Hurley, L. and Needham-Vandevanter, D., "Covalent Binding of Antitumor Antibiotics in the Minor Groove of DNA. Mechanism of Action of CC-1065 and the Pyrrolo(1,4)benzodiazepines," Acc. Chem. Res., 19, 230-237 (1986).
Itoh et al., "Sibanomicin, a new pyrrolo(1,4)benzodiazepine antitumor antibiotic produced by a Micromonospora sp." J. Antibiotics, 41, 1281-1284 (1988).
Kamal, A. et al., "Design, synthesis and evaluation of new noncrosslinking pyrrolobenzodiazepine dimers with efficient DNA binding ability and potent antitumor activity," J. Med. Chem. (2002) 45:4679-4688.
Kaneko, T. et al., "Bicyclic and tricyclic analogues of anthramycin," J. Med. Chem. (1985) 28:388-392.
Kohn, K., "Anthramycin," Antibiotics III, Springer-Verlag, NY, 3-11 (1975).
Konishi, M. et al., "Chicamycin, a new antitumor antibiotic II. Structure determination of chicamycins A and B," J. Antibiotics, 37, 200-206 (1984).
Kunimoto et al., "Mazethramycin, a new member of anthramycin group antibiotics," J. Antibiotics, 33, 665-667 (1980).
Langley, D.R. and Thurston, D.E., "A versatile and efficient synthesis of carbinolamine-containing pyrrolo[1,4]benzodiazepines via the cyclization of N-92-aminobenzoyl)pyrrolidine-2-carboxaldehyde diethyl thioacetals: total synthesis of prothracarcin," J. Org. Chem., 52, 91-97 (1987).
Langlois, N. et al., "Synthesis and cytotoxicity on sensitive and doxorubicin-resistant cell lines of new pyrrolo[2,1-c][1,4]benzodiazepines related to anthramycin," J. Med. Chem. (2001) 44:3754-3757.
Leber, J.D. et al., "A revised structure for sibiromycin," J. Am. Chem. Soc., 110, 2992-2993 (1988).
Leimgruber, W. et al., "Isolation and characterization of anthramycin, a new antitumor antibiotic," J. Am. Chem. Soc., 87, 5791-5793 (1965).
Leimgruber, W. et al., "The structure of anthramycin," J. Am. Chem. Soc., 87, 5793-5795 (1965).
Shimizu, K et al., "Prothracarcin, a Novel Antitumor Antibiotic," J. Antibiotics, 35, 972-978 (1982).
Takeuchi, T. et al., "Neothramycins A and B, New Antitumor Antibiotics," J. Antibiotics, 29, 93-96 (1976).
Thurston, D.E. and Bose, D.S., "Synthesis of DNA-Interactive Pyrrolo[2,1-c][1,4]benzodiazepines," Chem. Rev., 94:433-465 (1994).
Thurston, D.E. and Thompson, A.S., "The molecular recognition of DNA," Chem. Brit., 26, 767-772 (1990).
Tsunakawa, M. et al., "Porothramycin, a new antibiotic of the anthramycin group: Production, isolation, structure and biological activity," J. Antibiotics, 41:1366-1373 (1988).
Umezawa, H. et al., Chemical Abstract No. 4427a, "Mazethramycins" Chemical Abstracts, vol. 90, No. 1, 428 (1979).
Weidner-Wells, M.A. et al., "Photochemical approach to the synthesis of the pyrrolo[1,4]benzodiazepine antibiotics," J. Org. Chem. (1989) 54:5746-5758.
Wolff, M.E., Burger's Medicinal Chemistry, 4th Edition, Part I, Wiley: New York (1979) 336-337.
Workman, P. et al., "United Kingdom Co-ordinating Committee on Cancer Research (UKCCCR) guidelines for the welfare of animals in experimental neoplasia (second edition)," Br. J. Cancer (1998) 77(1):1-10.
Xie, G. et al., "Bisindolylmaleimides linked to DNA minor groove binding lexitropsins: synthesis, inhibitory activity against topoisomerasel, and biological evaluation," J. Med. Chem. (1996) 39:1049-1055.
United States Office Action for U.S. Appl. No. 09/763,813 dated Sep. 10, 2002 (11 pages).
United States Office Action for U.S. Appl. No. 09/763,813 dated Feb. 28, 2003 (8 pages).
United States Office Action for U.S. Appl. No. 09/763,813 dated May 21, 2003 (7 pages).
United States Office Action for U.S. Appl. No. 09/763,767 dated May 23, 2002 (20 pages).
United States Office Action for U.S. Appl. No. 09/763,767 dated Nov. 15, 2002 (19 pages).
United States Office Action for U.S. Appl. No. 09/763,767 dated May 20, 2003 (11 pages).
United States Office Action for U.S. Appl. No. 09/763,767 dated Jan. 14, 2004 (11 pages).

United States Office Action for U.S. Appl. No. 09/763,767 dated Aug. 4, 2004 (7 pages).
United States Office Action for U.S. Appl. No. 09/763,767 dated Jun. 9, 2005 (5 pages).
United States Office Action for U.S. Appl. No. 11/367,241 dated Jun. 22, 2006 (11 pages).
United States Office Action for U.S. Appl. No. 11/367,241 dated Nov. 24, 2006 (16 pages).
United States Office Action for U.S. Appl. No. 09/763,814 dated Sep. 13, 2001 (16 pages).
United States Office Action for U.S. Appl. No. 09/763,814 dated Apr. 23, 2002 (23 pages).
United States Office Action for U.S. Appl. No. 09/763,814 dated Jul. 24, 2002 (8 pages).
United States Office Action for U.S. Appl. No. 09/763,814 dated Sep. 23, 2002 (8 pages).
United States Office Action for U.S. Appl. No. 09/673,768 dated Dec. 14, 2001 (7 pages).
United States Office Action for U.S. Appl. No. 09/673,768 dated Jul. 12, 2002 (4 pages).
United States Office Action for U.S. Appl. No. 09/673,768 dated Dec. 24, 2002 (4 pages).
United States Office Action for U.S. Appl. No. 10/021,213 dated May 20, 2003 (10 pages).
United States Office Action for U.S. Appl. No. 10/379,049 dated Mar. 21, 2005 (14 pages).
United States Office Action for U.S. Appl. No. 10/379,049 dated Oct. 5, 2005 (17 pages).
United States Office Action for U.S. Appl. No. 10/379,049 dated Apr. 26, 2006 (9 pages).
United States Office Action for U.S. Appl. No. 10/602,521 dated Sep. 24, 2007 (12 pages).
United States Office Action for U.S. Appl. No. 10/602,521 dated Mar. 26, 2008 (8 pages).
United States Office Action for U.S. Appl. No. 10/602,521 dated May 31, 2008 (8 pages).
United States Office Action for U.S. Appl. No. 10/602,521 dated Jul. 15, 2008 (7 pages).
United States Office Action for U.S. Appl. No. 10/602,521 dated Dec. 10, 2008 (12 pages).
United States Office Action for U.S. Appl. No. 10/824,743 dated Jul. 31, 2006 (6 pages).
United States Office Action for U.S. Appl. No. 10/824,743 dated Jan. 17, 2007 (15 pages).
United States Office Action for U.S. Appl. No. 10/824,743 dated Oct. 9, 2007 (12 pages).
United States Office Action for U.S. Appl. No. 10/534,825 dated Sep. 7, 2006 (7 pages).
United States Office Action for U.S. Appl. No. 10/534,825 dated Mar. 2, 2007 (7 pages).
United States Office Action for U.S. Appl. No. 10/534,825 dated Sep. 20, 2007 (4 pages).
United States Office Action for U.S. Appl. No. 10/571,274 dated Oct. 31, 2007 (6 pages).
United States Office Action for U.S. Appl. No. 10/598,470 dated May 23, 2008 (6 pages).
United States Office Action for U.S. Appl. No. 10/598,482 dated May 22, 2008 (9 pages).
United States Office Action for U.S. Appl. No. 10/598,482 dated Nov. 24, 2008 (6 pages).
United States Office Action for U.S. Appl. No. 10/598,691 dated Mar. 21, 2008 (7 pages).
United States Office Action for U.S. Appl. No. 10/598,691 dated Sep. 29, 2008 (6 pages).
United States Office Action for U.S. Appl. No. 11/569,007 dated Oct. 15, 2008 (12 pages).
United States Office Action for U.S. Appl. No. 10/598,518 dated Mar. 13, 2009 (7 pages).
United States Office Action for U.S. Appl. No. 11/569,007 dated Jun. 1, 2009 (10 pages).
United States Office Action for U.S. Appl. No. 10/591,140 dated Jul. 6, 2009 (17 pages).
United States Office Action for U.S. Appl. No. 10/602,521 dated Sep. 9, 2009 (14 pages).
United States Office Action for U.S. Appl. No. 10/598,518 dated Sep. 28, 2009 (6 pages).
United States Patent Office Action for U.S. Appl. No. 10/591,140 dated Jan. 19, 2010 (7 pages).
United States Patent Office Action for U.S. Appl. No. 12/610,478 dated Aug. 6, 2010 (14 pages).
United States Patent Office Action for U.S. Appl. No. 12/089,459 dated Oct. 14, 2010 (13 pages).
United States Patent Office Action for U.S. Appl. No. 12/089,459 dated Apr. 12, 2011 (7 pages).
United States Patent Office Action for U.S. Appl. No. 10/591,140 dated Dec. 6, 2010 (7 pages).
United States Patent Office Action for U.S. Appl. No. 12/610,478 dated Dec. 17, 2010 (5 pages).
International Search Report and Written Opinion for Application No. PCT/GB2009/001819 dated Oct. 29, 2009 (8 pages).
International Search Report and Written Opinion for Application No. PCT/US2011/032668 dated May 26, 2011 (12 pages).
United States Patent Office Action for U.S. Appl. No. 12/610,478 dated Jul. 22, 2011 (7 pages).
Banker, G.S. et al., Modern Pharmaceutics, Third Edition, Marcel Dekker, New York (1996) 451 and 596.
Dorwald, F.Z., Side Reactions in Organic Synthesis: a Guide to Successful Synthesis Design, Weinheim: Wiley-VCH Verlag GmbH and Co., KGaA (2005) Preface.
Gavezzotti, A., "Are crystal structures predictable?" Acc. Chem. Res. (1994) 27:309-314.
Jordan, V.C., "Tamoxifen: a most unlikely pioneering medicine," Nature Reviews: Drug Discovery (2003) 2:205-213.
Souillac, P. et al., "Characterization of delivery systems, differential scanning calorimetry," Encyclopedia of Controlled Drug Delivery (1999) 212-227.
Vippagunta, S.R. et al., "Crystalline solids," Adv. Drug Delivery Rev. (2001) 48:3-26.
Wolff, M.E., Burger's Medicinal Chemistry, 5th Edition, Part I, John Wiley & Sons, New York (1995) 975-977.
United States Patent Office Action for U.S. Appl. No. 13/041,849 dated Dec. 1, 2011 (24 pages).
United States Patent Office Action for U.S. Appl. No. 12/089,459 dated Aug. 17, 2011 (3 pages).

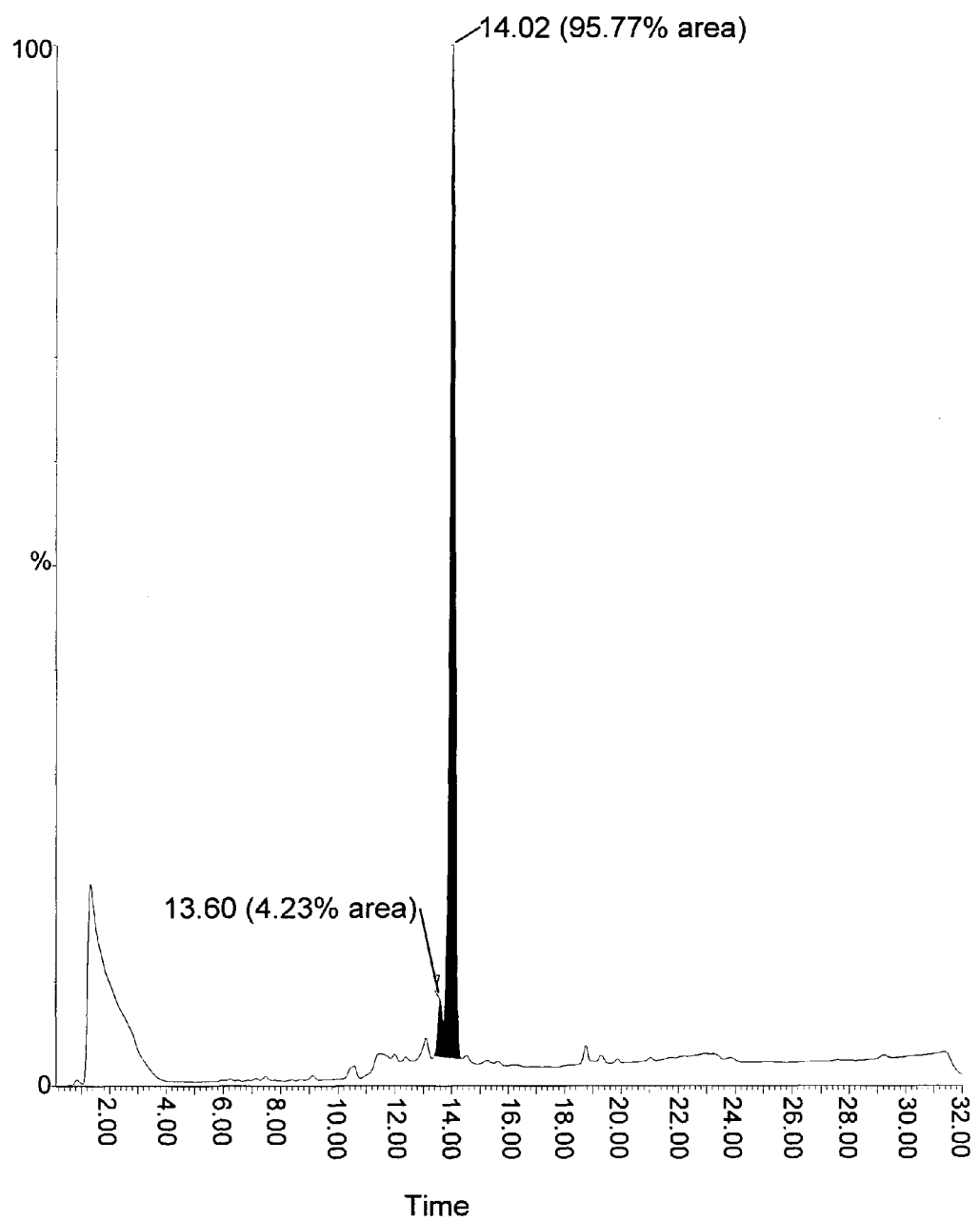

PYRROLOBENZODIAZEPINES

CROSS-REFERENCE TO RELATED APPLICATIONS

This patent application is a national stage filing under 35 U.S.C. 371 of International Application No. PCT/GB2009/001819, filed on Jul. 22, 2009, which claims foreign priority benefits to United Kingdom Patent Application No. 0813432.2, filed Jul. 22, 2008, which are incorporated herein by reference in their entities.

The present invention relates to pyrrolobenzodiazepines (PBDs), and in particular pyrrolobenzodiazepine dimers bearing C2 aryl substitutions.

BACKGROUND TO THE INVENTION

Some pyrrolobenzodiazepines (PBDs) have the ability to recognise and bond to specific sequences of DNA; the preferred sequence is PuGPu. The first PBD antitumour antibiotic, anthramycin, was discovered in 1965 (Leimgruber, et al., *J. Am. Chem. Soc.*, 87, 5793-5795 (1965); Leimgruber, et al., *J. Am. Chem. Soc.*, 87, 5791-5793 (1965)). Since then, a number of naturally occurring PBDs have been reported, and over 10 synthetic routes have been developed to a variety of analogues (Thurston, et al., *Chem. Rev.* 1994, 433-465 (1994)). Family members include abbeymycin (Hochlowski, et al., *J. Antibiotics*, 40, 145-148 (1987)), chicamycin (Konishi, et al., *J. Antibiotics*, 37, 200-206 (1984)), DC-81 (Japanese Patent 58-180 487; Thurston, et al., *Chem. Brit.*, 26, 767-772 (1990); Bose, et al., *Tetrahedron*, 48, 751-758 (1992)), mazethramycin (Kuminoto, et al., *J. Antibiotics*, 33, 665-667 (1980)), neothramycins A and B (Takeuchi, et al., *J. Antibiotics*, 29, 93-96 (1976)), porothramycin (Tsunakawa, et al., *J. Antibiotics*, 41, 1366-1373 (1988)), prothracarcin (Shimizu, et al, *J. Antibiotics*, 29, 2492-2503 (1982); Langley and Thurston, *J. Org. Chem.*, 52, 91-97 (1987)), sibanomicin (DC-102)(Hara, et al., *J. Antibiotics*, 41, 702-704 (1988); Itoh, et al., *J. Antibiotics*, 41, 1281-1284 (1988)), sibiromycin (Leber, et al., *J. Am. Chem. Soc.*, 110, 2992-2993 (1988)) and tomamycin (Arima, et al., *J. Antibiotics*, 25, 437-444 (1972)). PBDs are of the general structure:

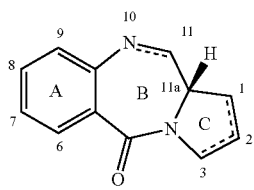

They differ in the number, type and position of substituents, in both their aromatic A rings and pyrrolo C rings, and in the degree of saturation of the C ring. In the B-ring there is either an imine (N═C), a carbinolamine (NH—CH(OH)), or a carbinolamine methyl ether (NH—CH(OMe)) at the N10-C11 position which is the electrophilic centre responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, In *Antibiotics III*. Springer-Verlag, New York, pp. 3-11 (1975); Hurley and Needham-VanDevanter, *Acc. Chem. Res.*, 19, 230-237 (1986)). Their ability to form an adduct in the minor groove, enables them to interfere with DNA processing, hence their use as antitumour agents.

The present inventors have previously disclosed, in WO 2004/043963, cytotoxic compounds having an aryl group at the C2 position, for example:

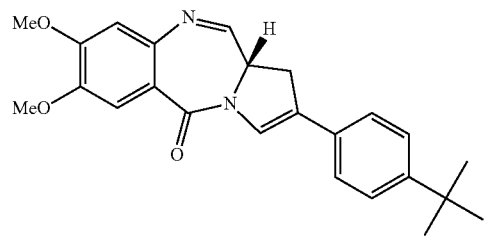 [SMILES: COc1cc2c(cc1OC)C(=O)N1C=C(c3ccc(C(C)(C)C)cc3)C[C@H]1C=N2]

The present inventors have also previously disclosed, in co-pending PCT application PCT/GB2005/000768 (published as WO 2005/085251), dimeric PBD compounds bearing C2 aryl substituents, such as:

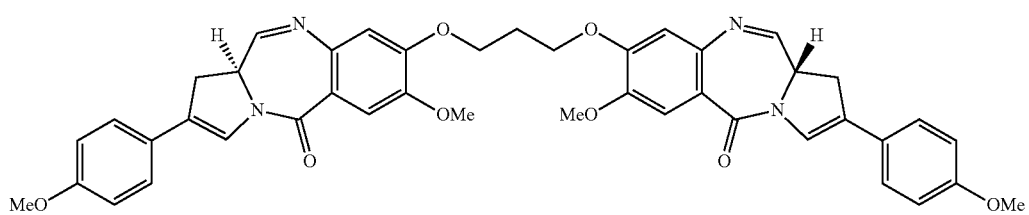

ZC-207

The present inventors encountered some issues with the solubility of compounds such as ZC-207, which they resolved by the use of a different form of these compounds. This form is disclosed in pending PCT application PCT/GB2006/001456 (published as WO 2006/111759). It discloses compounds with the formula I:

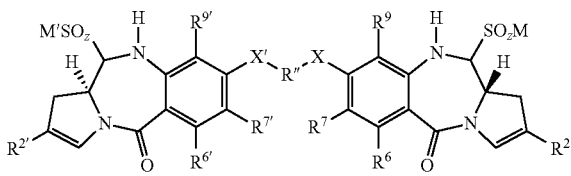

or solvate thereof, wherein:

$R^2$ is an optionally substituted $C_{5-20}$ aryl group;

$R^6$ and $R^9$ are independently selected from H, R, OH, OR, SH, SR, $NH_2$, NHR, NRR', nitro, $Me_3Sn$ and halo;

where R and R' are independently selected from optionally substituted $C_{1-12}$ alkyl, $C_{3-20}$ heterocyclyl and $C_{5-20}$ aryl groups;

$R^7$ is selected from H, R, OH, OR, SH, SR, $NH_2$, NHR, NHRR', nitro, $Me_3Sn$ and halo;

R" is a $C_{3-12}$ alkylene group, which chain may be interrupted by one or more heteroatoms, e.g. O, S, NH, and/or aromatic rings, e.g. benzene or pyridine;

X is selected from O, S, or NH;

z is 2 or 3;

M is a monovalent pharmaceutically acceptable cation;

$R^{2'}$, $R^{6'}$, $R^{7'}$, $R^{9'}$, X' and M' are selected from the same groups as $R^2$, $R^6$, $R^7$, $R^9$, X and M respectively, or M and M' may together represent a divalent pharmaceutically acceptable cation.

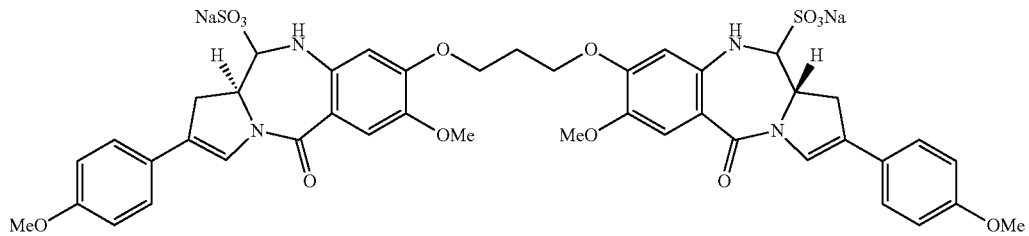

ZC-423

Pyrrolobenzodiazepines having an imine bond are known to convert to the di-carbinolamine form in water, and isolated pyrrolobenzodiazepines often exist as a mixture of the imine, mono-carbinolamine and di-carbinolamine forms. Furthermore, if the compound is isolated as a solid with a mixture of these three forms, the balance between them may change over time. Although this does not pose a problem for administration of the compound, it can provide difficulties in accurately assessing the amount of active substance in a given amount of powder. Compounds of the type disclosed in WO 2006/111759, at least to some extent, overcome this difficulty whilst remaining active, and are thus suited to formulation as pharmaceuticals.

Dimeric pyrrolobenzodiazepines offer advantages over monomeric pyrrolobenzodiazepines in that they possess the ability to cross-link DNA in the minor groove, which can lead to an increase in cytotoxicity.

A particularly advantageous compound in this class is disclosed in WO 2006/111759 as ZC-423, and shown below.

This compound is synthesised in WO 2006/111759 as Example 1.

However, the present inventors have found difficulties with this synthesis. In WO 2006/111759 the synthesis comprised a very large number of steps, which decreased the potential yield as well as adding to the experimental difficulty of synthesising the product.

There is a need therefore for an improved method of preparing ZC-423 that has fewer steps and provides an increased yield of the final product.

SUMMARY OF THE INVENTION

In a general aspect, the present invention provides novel intermediates for use in the preparation of ZC-423 and precursors thereof. The present invention also provides methods for the preparation of ZC-423 and the precursors thereof.

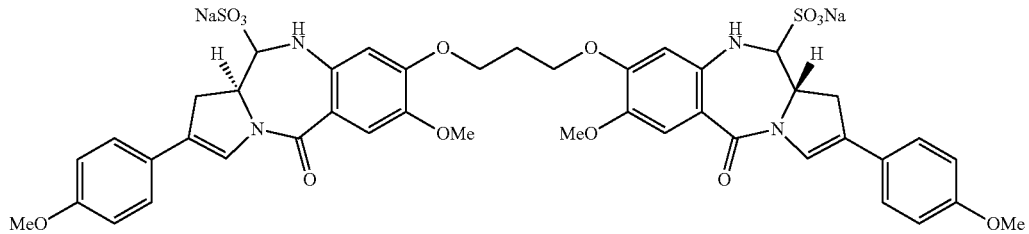

ZC-423

In a first aspect of the present invention there is provided a method of preparing ZC-423, the method comprising the step of treating compound (14) with a biphasic solvent mixture comprising sodium bisulphite, wherein the biphasic solvent mixture comprises an aqueous solution of the bisulphite salt and an organic solvent that is immiscible with the aqueous solution, and compound (14) is treated with the bisulphite salt for 12 hours or more As an alternative aspect of the present invention, there is provided a method of preparing ZC-423 comprising the step of treating compound (14) with a solvent mixture comprising sodium bisulphite salt. The solvent mixture comprises an aqueous solution of the bisulphite salt and an organic solvent that is miscible with the aqueous solution. The organic solvent may be a protic solvent, and is preferably an alkyl alcohol, such as isopropylalcohol (IPA).

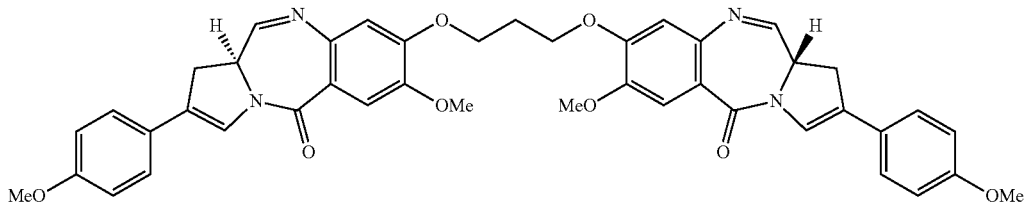

14

In a second aspect of the invention there is provided a method of preparing compound (14), the method comprising the step of reacting compound (13). Preferably compound (13) is reacted with a reducing agent.

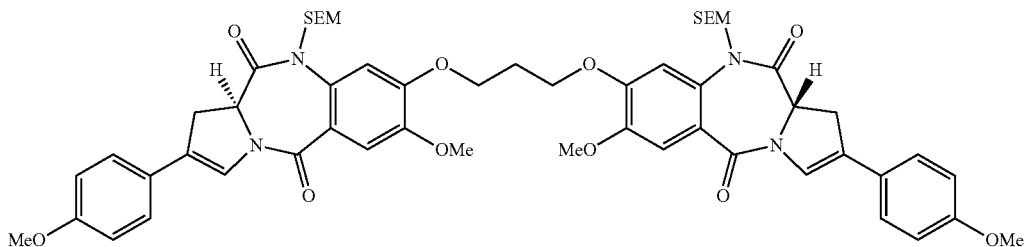

13

In a third aspect of the present invention there is provided a method of preparing compound (13), the method comprising the step of reacting compound (12) with methoxyphenylboronic acid. Preferably the reaction is performed in the presence of a palladium complex and a base.

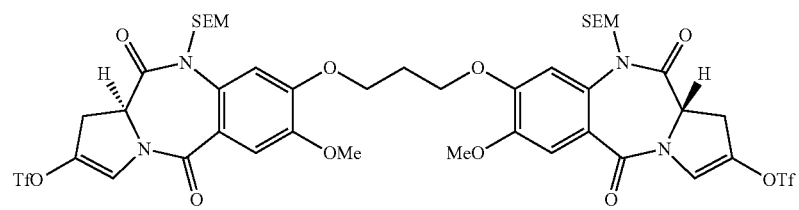

12

In a fourth aspect of the invention there is provided a method of preparing compound (12), the method comprising the step of reacting compound (11). Preferably compound (11) is reacted with triflic anhydride in the presence of 2,6-lutidine.

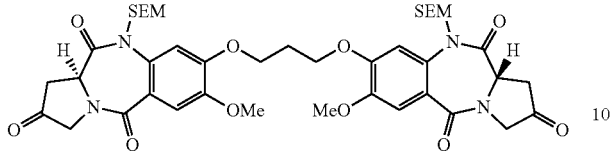

11

In a fifth aspect of the present invention there is provided a method of preparing compound (11), the method comprising the step of oxidising compound (10). Preferably compound (10) is oxidised with TEMPO.

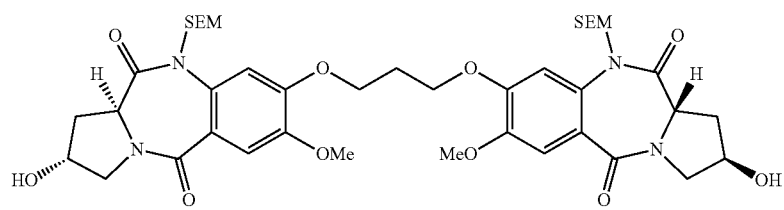

10

In a sixth aspect of the present invention there is provided a method of preparing compound (10), the method comprising the step of removing the hydroxy-protecting groups of compound (9). Preferably compound (9) is deprotected with TBAF.

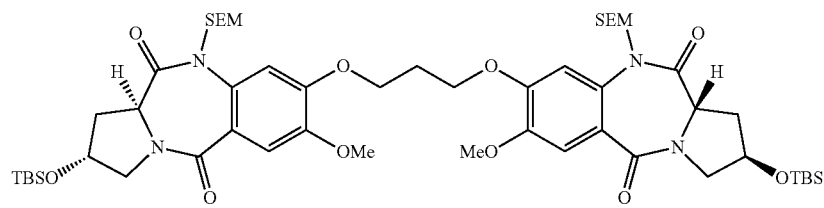

9

In a seventh aspect of the present invention there is provided a method of preparing compound (9), the method comprising the step of protecting the amide nitrogen atoms of compound (8) with SEM. Preferably compound (8) is treated with SEM-Cl in the presence of base. The base may be n-BuLi.

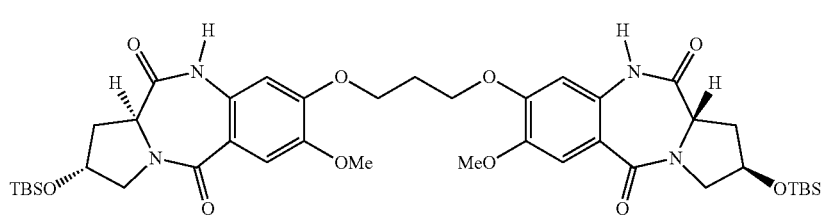

8

In an eighth aspect of the present invention there is provided a method of preparing compound (8), the method comprising the step of protecting the hydroxy groups of compound (7) with TBS.

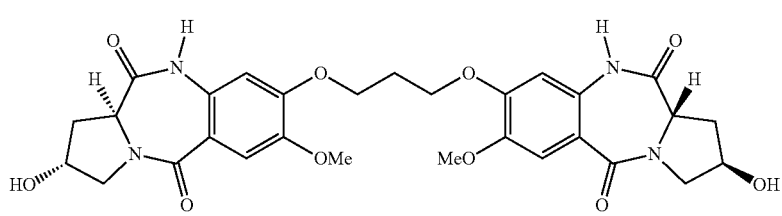

7

In a ninth aspect of the present invention there is provided a method of preparing compound (7), the method comprising the step of cyclising compound (6).

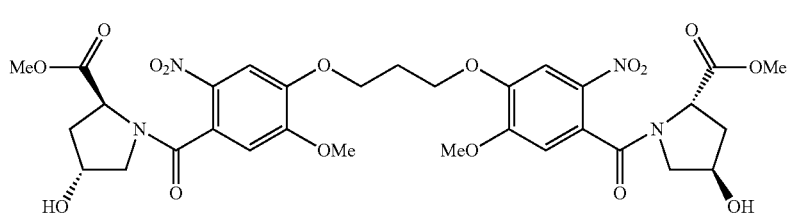

6

In a tenth aspect of the present invention there is provided a method of preparing compound (6), the method comprising the step of coupling compound (5) with methyl-4-hydroxy-pyrrolidine-2-carboxylate.

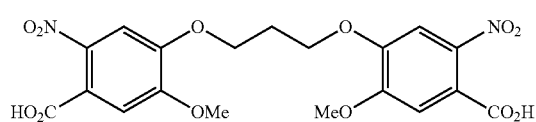

5

In another aspect of the invention there is provided a method of preparing ZC-423 comprising one or more of the methods of the first to tenth aspects of the invention.

The invention also provides the compound of formula (13).

The invention also provides the use of one or more of compounds (6), (7), (8), (9), (10), (11), (12) and (13) as intermediates for the preparation of compound (14) or ZC-423.

DESCRIPTION OF THE FIGURES

FIG. 2 is the LCMS of ZC-423 (SG-2285) as prepared on a gram scale by another of the methods described herein. The minor peak ($R_t$=13.82 min) corresponds to the S,S-form of ZC-423, and the major peak ($R_t$=14.38 min) corresponds to the S,R-form of ZC-423, as produced in the bisulphite salt addition reaction using a biphasic mixture comprising an aqueous solution of the bisulphite salt and an organic solvent that is immiscible with the aqueous solution.

DETAILED DESCRIPTION OF THE INVENTION

Figure 1:
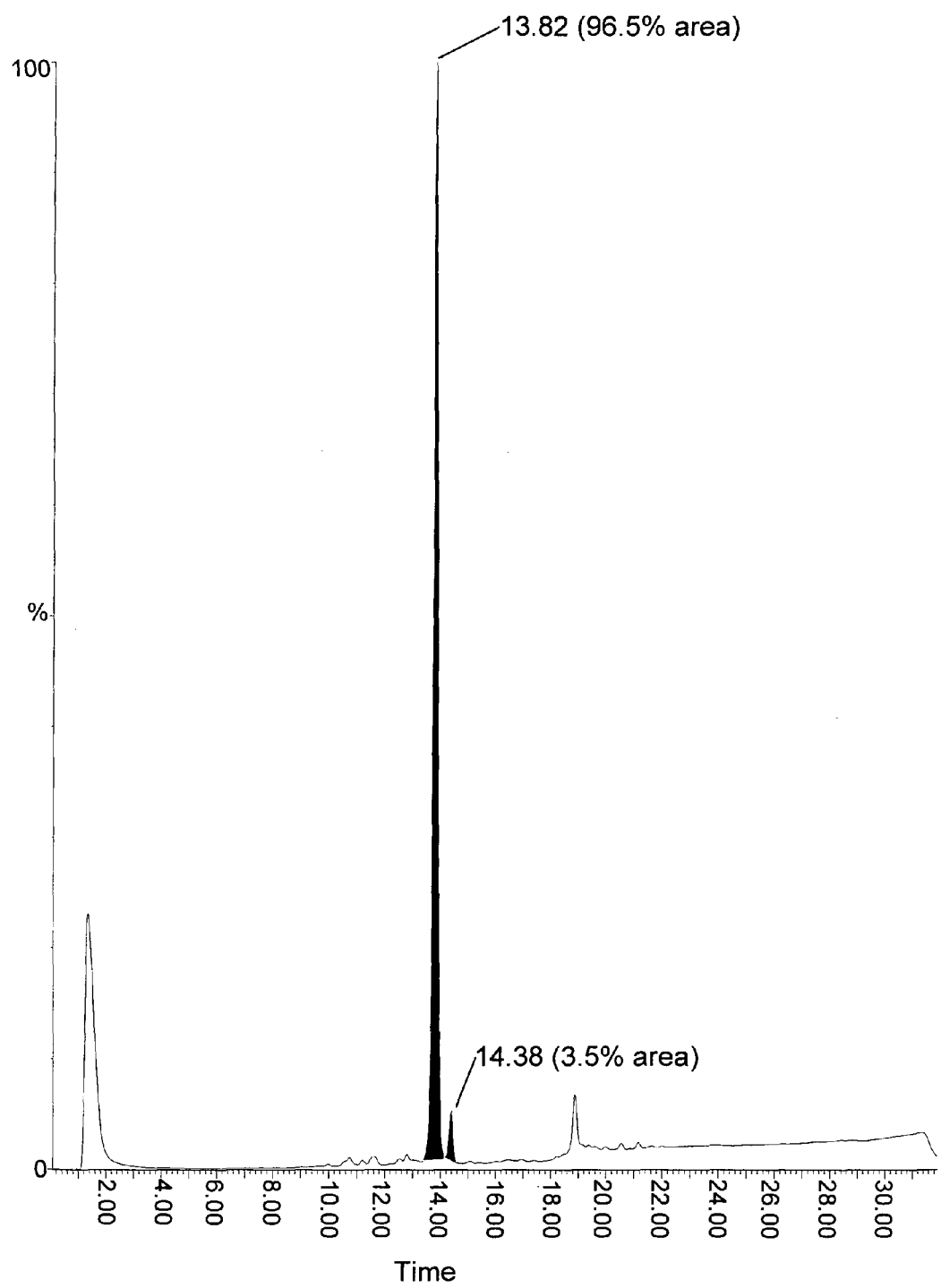
FIG. 1 is the LCMS of ZC-423 (SG-2285) as prepared on a gram scale by one of the methods described herein. The major peak ($R_t$=13.82 min) corresponds to the S,S-form of ZC-423 as produced in the bisulphite salt addition reaction using a solvent mixture comprising an aqueous solution of the bisulphite salt and an organic solvent that is miscible with the aqueous solution. The minor peak ($R_t$=14.38 min) corresponds to the S,R-form of ZC-423.

The present invention provides improved methods for the synthesis of ZC-423. The invention also provides novel intermediates for use in such methods. These methods allow ZC-423 to be prepared in higher yield and in less time compared to the methods that have been previously described for the preparation of this compound.

ZC-423

In one aspect of the present invention there is provided a method of preparing ZC-423, the method comprising the step of treating compound (14) with a solvent mixture comprising sodium bisulphite salt. The solvent mixture may comprise an aqueous solution of the bisulphite salt and an organic solvent that is miscible with the aqueous solution. The organic solvent may be a protic solvent. Preferably the protic solvent is an alkyl alcohol. The solvent is preferably propyl alcohol, most preferably isopropylalcohol (IPA). Compound (14) may be suspended in the solvent mixture.

Methanol may be used as the organic solvent although this is less preferred owing to toxicity issues.

The product of the reaction, ZC-423, may be dissolved in the solvent mixture. The starting material (compound (14)) typically remains as a solid suspended in the solvent mixture and may be collected by filtration during the reaction work up. Any unreacted starting material (14) that is isolated may be treated with a bisulphite salt for a second time to increase the yield of final product.

The bisulphite addition reaction may also be performed using a biphasic mixture comprising an organic solvent and an aqueous solution comprising the bisulphite salt. The organic solvent is immiscible with the aqueous solution. The organic solvent may be a solvent that dissolves compound (14). The organic solvent may be DCM. This reaction was previously reported in WO 2006/111759.

The yield for the bisulphite addition reaction is increased substantially when compound (14) is treated with a solvent mixture comprising a bisulphite salt, wherein the solvent mixture comprises an aqueous solution of the bisulphite salt and an organic solvent that is miscible with the aqueous solution. The yield for the improved reaction is 82% compared to the yield of 55% reported in WO 2006/111759.

However, the inventors have been able to improve on the yield recorded in WO 2006/111759 for the biphasic mixture. A longer reaction time is found to increase the yield. The preferred reaction times are discussed below. Also a careful work-up procedure including a rapid freezing step of the aqueous solvent phase provides an increased yield of 62% for this method.

In both the biphasic and miscible solvent systems, the ZC-423 product is obtained as a mixture of the S,S-diastereomer and S,R-diastereomer forms. The S and R notation refers to the stereochemistry at the C-11 centre of each benzodiazepine ring. The inventors have ascertained that no significant amount of R,R-diastereomer is produced in the addition reaction.

Unless otherwise explicitly stated, the use of the term "S,R-diastereomer" refers to ZC-423 as drawn herein where the C-11 centre of the left-hand benzodiazepine ring has an S-configuration and the C-11 centre of the right-hand benzodiazepine ring has an R-configuration, and where the C-11 centre of the left-hand benzodiazepine ring has an R-configuration and the C-11 centre of the right-hand benzodiazepine ring has an S-configuration. Due to the symmetrical nature of ZC-423, the S,R-diastereomer and R,S-diastereomer are the same.

The right-hand benzodiazepine ring within ZC-423 is shown below for reference where the C-11 centre is in the S-configuration.

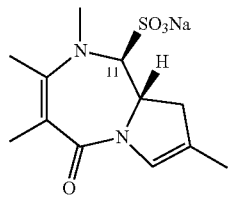

The predominance of the S,S-diastereomer or the S,R-diastereomer in the ZC-423 product is determined by the choice of solvent in the bisulphite addition reaction.

The inventors have established that the S,S-diastereomer is favoured where the bisulphite addition is performed in a solvent mixture comprising an aqueous solution of the bisulphite salt and an organic solvent that is miscible with the aqueous solution.

Where IPA is used as the organic solvent, the amount of the S,S-diastereomer in the product is found to be above 96%, with less than 4% of the S,R-diastereomer.

The inventors have established that the S,R-diastereomer is favoured where the bisulphite addition is performed in a biphasic mixture comprising an aqueous solution of the bisulphite salt and an organic solvent that is immiscible with the aqueous solution.

Where DCM is used as an organic solvent, the amount of S,R-diastereomer in the product is found to be around 90%, with around 10% of the S,S-diastereomer. Such a high proportion of the S,R-diastereomer is only possible where the preferred reaction conditions as described herein are used. In particular, a reaction time of 12 hours or more, more preferably 24 hours or more may be required. Furthermore, the aqueous solution comprising the reaction product may require freezing immediately upon completion of the addition reaction.

Without wishing to be bound by theory, the inventors believe that the biphasic reaction conditions favour a thermodynamic product (the S,R-diastereomer), whilst the addition reaction conditions that utilise an organic solvent that is miscible with the aqueous solution favour a kinetic product (the S,S-diastereomer).

The inventors have found that the bisulphite addition described previously in WO 2006/111759, which uses a DCM-based biphasic reaction mixture, results in a ZC-423 product having around 66% of the S,R-diastereomer and around 33% of the S,S-diastereomer. The inventors have established that the amount of S,R-diastereomer in the ZC-423 product may be increased by increasing the bisulphite addition reaction time. This is believed to favour the thermodynamic product.

In one embodiment, the method comprises the step of separating the S,S-diastereomer from the S,R-diastereomer. This method may involve liquid chromatography.

The present invention also provides compound ZC-423 comprising predominantly the S,S-diastereomer or the S,R-diastereomer.

In one embodiment compound ZC-423 comprises 70% or more, 80% or more or 90%, or more of the S,S-diastereomer.

In another embodiment compound ZC-423 comprises 70% or more, 80% or more, or 90% or more of the S,R-diastereomer.

The reaction of compound (14) with a bisulphite salt in a biphasic solvent system is described in WO 2006/111759. The stereochemistry at the C-11 centres is not given. Repeating the reaction as described therein, the inventors have subsequently established that the reaction product comprises 66% of the S,R-diastereomer and around 33% of the S,S-diastereomer.

WO 2006/111759 also describes the synthesis of an analogue of ZC-423, compound 47, having a five-carbon linker between the pyrrolobenzodiazepine moieties. The stereochemistry of the C-11 centres of the product is given as S,S. There is no indication as to how this product stereochemistry was assigned, or the ratio of products in the reaction mixture.

$^1$H NMR analysis of a separated ZC-423 product may be used to determine the stereochemistry of each separated diastereomer. Liquid chromatography techniques have been found to be suitable for use in the separation of S,S- and S,R-diastereomers. The methods described herein allow the production of one diastereomer in large excess over the other diastereomer. The products of these methods may be analysed directly by NMR to determine the identity of the predominant diastereomer. Previously, when the product mixture comprised comparable amounts of each diastereomer, the NMR analysis of the mixed product could not easily be used to identify the major product.

The present invention also provides a method of preparing a compound having 70% or more, 80% or more or 90%, or more of the S,S- or the S,R-diastereomer.

A method of preparing a S,S-diastereomer may comprise the step of treating compound (14) with a bisulphite salt in a solvent mixture comprising an aqueous solution of the bisulphite salt and an organic solvent that is miscible with the aqueous solution, as described above.

Thus, another aspect of the present invention provides a method of preparing a S,R-diastereomer may comprise the step of treating compound (14) with a bisulphite salt for 12 hours or more, or, most preferably, 24 hours or more. A biphasic solvent system as described herein may be used.

A method of preparing a S,R-diastereomer may comprise the step of treating compound (14) with a bisulphite salt for 4 hours or less, 2 hours or less, or, most preferably 1 hour or less. A solvent system comprising a miscible organic solvent as described herein may be used.

For both the biphasic solvent mixture-based addition reaction and the miscible solvent mixture-based addition reaction, the ratio of S,S- to S,R-diastereomer in the ZC-423 product is observed to alter during the reaction work-up. However, the ratio of the diastereomer may be preserved, or the alteration minimised, if compound ZC-423 is purified by the methods described herein. In particular, it has been found that the alteration in the ratio of diastereomers may be limited or prevented by freezing the product in a solvent immediately upon, or soon after, completion of the addition reaction. The solvent is typically a solvent used in the addition reaction and may be the actual solvent used in the addition reaction.

In the addition reaction using a miscible organic solvent, the reaction solvent mixture may be frozen soon after the reaction is deemed complete e.g. by LCMS or TLC. Alternatively, the reaction solvent mixture may be frozen soon after the mixture has been filtered to remove insoluble impurities (such as unreacted starting material).

In the addition reaction using an immiscible organic solvent, a reaction solvent containing ZC-423 may be frozen soon after the organic phase and the aqueous phase of the biphasic solvent mixture are separated. ZC-423 is typically contained in the aqueous phase, and it is this solvent that may be frozen soon after separation from the organic phase or soon after any appropriate extraction and washing steps.

Thus the present invention provides a process of preparing ZC-423, the process comprising the step of freezing a solvent comprising ZC-423 soon after the reaction producing ZC-423 is deemed complete.

The term "soon after" may be interpreted as meaning 5 minutes or less, 15 minutes or less, 30 minutes or less, or 60 minutes or less after the event described.

A solvent may be frozen by reducing the temperature of the solvent to 0° C. or below, −10° C. or below, −70° C. or below, −100° C. or below, or −190° C. or below. Suitable cooling techniques using appropriate cooling baths are well known to the skilled chemist. It is preferred that the solvent is frozen by reducing the temperature of the solvent to −190° C. or below. This may be achieved using a liquid nitrogen bath.

The solvent is taken to a temperature that is suitable for freeze drying the material.

After filtration of the reaction mixture to remove unreacted starting material, where necessary, or separation of the solvent phases, where necessary, a reaction solvent is frozen, preferably using a liquid nitrogen bath, and freeze dried. The solvent is preferably dried over a period of 1 to 5 days, preferably for a period of around 3 days.

It is preferred that the frozen solvent is initially kept at around −190° C. or below until the majority of the organic solvent, if present, is removed.

After the solution is frozen it is freeze dried. The frozen solution may be maintained at the frozen temperature during drying, then allowed to warm (whilst still drying). Preferably the frozen solution is maintained at around −190° C. or below for at least 3 hours before being allowed to warm.

The freeze drying process yields ZC-423 substantially free of solvent.

The material that results from the freeze drying step (typically a foam) may be taken up in an organic solvent, preferably ethyl acetate. The resulting suspension may then be filtered, washed with further solvent, and dried to give the ZC-423 product in substantially pure form.

Compound (14)

The present invention provides the use of the compound of formula (14) in the preparation of ZC-423.

Compound (14) may be prepared from compound (13), including reacting compound (13) with a reducing agent.

The reducing agent may be selected from $LiBH_4$ and $NaBH_4$. Preferably the reducing agent is $LiBH_4$.

After treatment of compound (13) with a reducing agent, a SEM deprotecting reagent may be added, where appropriate. The SEM deprotecting reagent is preferably an acid, and most preferably an organic acid. The inventors have found that formic acid may be used to good effect, providing a yield of 58%. Citric acid provides even greater yields (75%). The use of organic acids such as citric and formic acid is more practicable on a large scale compared with silica.

In an alternative embodiment, silica gel may be used as the SEM deprotecting reagent. Silica gel may be used to generate the product in greater yield (98%) in comparison to the yields for the formic acid and citric acid mediated reactions.

The preparation of compound (14) from compound (13) may proceed via intermediate (13b).

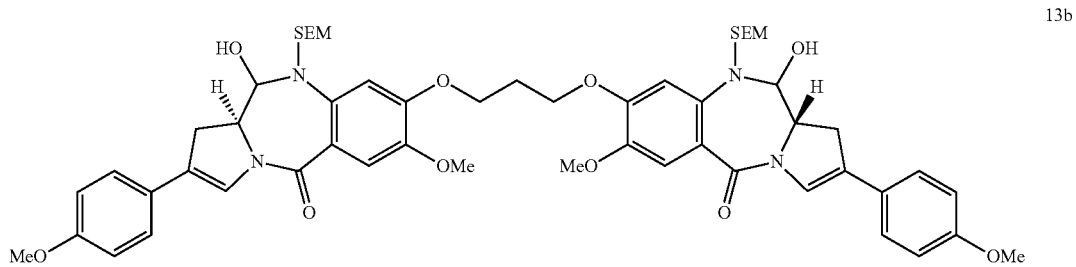 [SMILES: COc1ccc(C2=CN3C(=O)c4cc(OC)c(OCCCOc5cc6c(cc5OC)C(=O)N5C=C(c7ccc(OC)cc7)C[C@H]5C(O)N6COCC[Si](C)(C)C)cc4N(COCC[Si](C)(C)C)C(O)[C@@H]3C2)cc1]

13b

Intermediate (13b) is prepared by reduction of compound (14). It is preferred that intermediate (13b) is not isolated, and is treated with a SEM deprotecting reagent after the reduction step to yield compound (14). Preferably compound (13b) is used within 24 hours of its preparation or isolation. Most preferably, intermediate (13b) is used within 4 hours, within 2 hours or within 1 hour of its preparation or isolation.

$LiBH_4$ is a stronger reducing agent than $NaBH_4$ and therefore allows the reduction reaction to proceed at a faster rate. As a consequence, the product 13b may be isolated sooner before it is converted to imine which is highly susceptible to over reduction.

Compound (13)

The present invention provides a compound of formula (13) for use in the preparation of compounds (14) or ZC-423.

Compound (13) may be prepared by reacting compound (12) with methoxyphenylboronic acid. Preferably the reaction is performed in the presence of a palladium complex and a base.

The palladium complex may be tetrakis(triphenylphosphine)palladium, $Pd[PPh_3]_4$.

The base may be a metal carbonate. The metal carbonate may be an alkali metal carbonate, preferably sodium carbonate.

The reaction is preferably performed under an oxygen-free atmosphere. The exclusion of oxygen maximises the yield of product material. A nitrogen atmosphere may be used.

The reaction may be performed at 30° C. or less. On related substrates, higher temperatures were found to induce base-mediated racemisation at the C11a position. Such racemisation has been observed on related substrates (see Antonow et al 2007).

The base may be an organic base. In one embodiment the base may be TEA.

The reaction product may be purified to remove partially-reacted material.

The yield for the coupling reaction of compound (13) with methoxyphenylboronic acid is the same (87%) as the corresponding reaction between methoxyphenylboronic acid and the triflate compound that has been previously described in the art (compound (20) shown below, as described in WO 2006/111759). The triflate compound previously described utilises a Troc protecting group rather than the SEM protecting group reported in the present synthesis. Furthermore, the triflate compound previously described has a silyl ether group where compound (13) contains a carbonyl functionality.

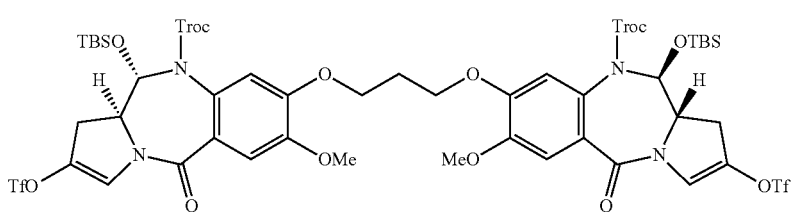

20

The change in coupling partner architecture does not reduce the yield of the coupling reaction.

Compound (12)

The present invention provides the use of compounds of formula (12) in the preparation of compounds (14) or ZC-423. Compound (12) also finds use in the preparation of compound (13).

Compound (12) may be prepared from compound formula (11). Preferably compound (11) is reacted with triflic anhydride in the presence of a base. The base may be an organic base. In one embodiment the organic base is selected from pyridine and 2,6-lutidine. Preferably the base is 2,6-lutidine.

The use of 2,6-lutidine gives superior yields in the triflation reaction compared to pyridine. The use of 2,6-lutidine gives a typical yield of 59%. The use of pyridine in the same reaction gives only a 39% yield of product.

In addition, the use of 2,6-lutidine significantly reduces the triflation reaction time. The optimum yield in the pyridine reaction is obtained after 6 hours, whilst the optimum yield in the 2,6-lutidine reaction is obtained after 1 hour.

The inventors have also established that further increases in yield may be obtained when the reaction is performed at reduced temperatures. At 0° C., the yield in the 2,6-lutidine reaction is 59% whilst repeating the reaction at −45° C. increases the yield to greater than 70%.

The organic base is preferably added to a solution of compound (11) at 0° C. or below, or −45° C. or below. The temperature of the solution should be maintained within 5° C. of the intended reaction temperature during the addition of the organic base.

Compound (11)

The present invention provides the use of compounds of formula (11) in the preparation of compounds (14) or ZC-423. Compound (11) may also find use in the preparation of compounds of formula (12) and (13).

Compound (11) may be prepared by oxidising compound (10). Preferably compound (10) is oxidised with TEMPO.

The TEMPO-mediated oxidation reaction may be performed in the presence of bleach. In one embodiment the bleach is TCCA.

In an alternative embodiment the bleach is a hypochlorite salt, most preferably sodium hypochlorite. When hypochlorite salt is added to the reaction mixture, the temperature of the reaction mixture is held in the range 0 to 5° C.

Compound (10) may be oxidised under Swern-type oxidation conditions. Thus compound (10) may be treated with a mixture of oxalyl chloride and DMSO. The oxalyl chloride and DMSO may be combined prior to the addition of compound (10). Subsequently a base may be added to the reaction mixture. The base may be an organic base, and is most preferably TEA.

Compound (10)

The present invention provides the use of compounds of formula (10) in the preparation of compounds (14) or ZC-423. Compound (10) may also find use in the preparation of compounds (11), (12) and (13).

Compound (10) may be prepared by removing the hydroxy-protecting group of compound (9). Preferably compound (9) is deprotected with TBAF.

Compound (9)

The present invention provides the use of compounds of formula (9) in the preparation of compounds (14) or ZC-423. Compound (9) may also find use in the preparation of compounds (10), (11), (12) and (13).

Compound (9) may be prepared by protecting the amide nitrogen atoms of compound (8) with SEM. Compound (8) may be treated with SEM-Cl in the presence of a base. The base may be n-BuLi. Compound (8) may be first treated with base. SEM-Cl may then be subsequently added. Alternatively, the base and SEM-Cl may be added to compound (8) at around the same time. The reaction may be performed in an ether solvent, preferably THF.

Compound (8)

The present invention provides the use of compounds of formula (8) in the preparation of compounds (14) or ZC-423. Compound (8) may also find use in the preparation of compounds (9), (10), (11), (12) and (13).

Compound (8) may be prepared from compound (7). The method of preparing compound (8) comprises the step of protecting the hydroxy groups of compound (7) with TBS. Preferably compound (7) is treated with TBS-Cl in the presence of base. Preferably the base is an organic base. The base may be imidazole.

Compound (7)

The present invention provides the use of compounds of formula (7) in the preparation of compounds (14) or ZC-423. Compound (7) may also find use in the preparation of compounds (8), (9), (10), (11), (12) and (13).

Compound (7) may be prepared from compound (6). The method of preparing compound (7) comprises the step of cyclising compound (6).

In a preferred embodiment of the invention, compound (6) may be treated with hydrogen in the presence of a catalyst. The catalyst may be a Pd/C catalyst. The reaction may be performed at greater than atmospheric pressure. Preferably the reaction is performed at 50 psi (~345 kPa). A Parr hydrogenation apparatus may be used.

Compound (6) may be first treated with hydrogen in the presence of the catalyst. Subsequently, hydrazine may be added. In one embodiment, the reaction mixture is purified to remove the catalyst before hydrazine is added to the reaction material. Typically, the reaction mixture is filtered to remove solid catalyst. A double filtration may be required to remove the majority of the catalyst material.

Hydrazine hydrate may be used in the reaction. The reaction may be performed at reflux. Ethanol may be used as a solvent for the reaction. It is preferred that the initial filtration of the reaction mixture is performed hot.

Alternatively, compound (6) may be treated with hydrazine in the presence of a Raney nickel catalyst. Preferably the reaction temperature is from 30 to 85° C., more preferably from 45 to 75° C., and most preferably 50 to 65° C.

Methanol may be used as a solvent in the reaction, in which case the reaction may be performed under reflux (~65° C.).

The inventors have established that the Raney nickel and hydrazine combination provides superior results compared to hydrogen with a Pd/C catalyst alone. Both methods provide improved yields compared to the sodium dithionite-mediated reaction described in WO 2006/111759 on an analogous nitro compound (compound (16) which is shown in the Preferred Strategies section below). A sodium dithionite-mediated reduction may find use in the present invention, though the methods described above are most preferred.

Previously, in WO 2004/04396 a reductive cyclisation was described using Pd/C with hydrogen followed by a HCl treatment step. This method may be adapted for the conversion of compound (6) to compound (7). However, this reaction may lead to racemisation of the product, and the methods described above are consequently preferred.

Compound (6)

The present invention provides the use of compounds of formula (6) in the preparation of compound (14) or ZC-423. Compound (6) may also find use in the preparation of compounds of formula (7), (8), (9), (10), (11), (12) and (13).

Compound (6) may be prepared from compound (5). Compound (6) may be prepared by coupling compound (5) with methyl-4-hydroxypyrrolidine-2-carboxylate. Preferably the carboxylate is (2S,4R)-methyl-4-hydroxypyrrolidine-2-carboxylate. Preferably the hydrochloride salt of the carboxylate is used. The para-toluenesulfonate (p-TSOH) salt may also be used, though this is less preferred.

Compound (6) may be first treated with an activating agent to give the corresponding acid chloride compound. This compound may be isolated and stored for later use. The acid chloride may then be added to methyl-4-hydroxypyrrolidine-2-carboxylate.

The activating agent is added to generate the active ester form of compound (5). Preferably the activating agent is oxalyl chloride.

Preferably the coupling reaction is performed in the presence of base. The base may be an organic base. TEA may be used.

The inventors have established that compound (6) may be used advantageously in the preparation of benzodiazepine-containing compounds from compound (5).

Compound (5) may be used as an intermediate for the synthesis of compound (7) and its analogues. In contrast with the route disclosed in WO 2006/111759, the benzodiazepine-containing compound of formula (8) may be accessed in two steps from compound (5) via compound (7). In contrast, WO 2006/111759 describes a preparation of a benzodiazepine-containing compound in five steps from compound (5).

Compound (5)

The synthesis of compounds of formula (5) is described in the applicant's earlier application, WO 2006/111759. The preparation of compound (5) as described therein is specifically incorporated by reference herein. Example 1 in this earlier application is particularly relevant. WO 00/012508 also describes the preparation of compound (5) and is hereby incorporated by reference.

Briefly, compound (5), is derived from compound (2).

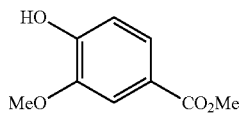
2

Compound (2) is dimerised to give compound (3).

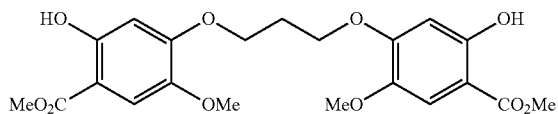
3

The hydroxyl groups on the dimer are then converted to nitro groups to yield compound (4).

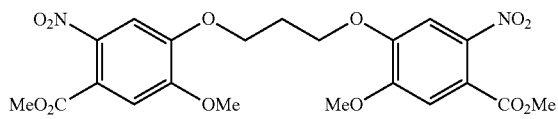
4

Compound (5) is obtained from (4) by hydrolysis of the methyl esters of compound (4).

In one embodiment of the invention, the preparation of any one of compounds (6) to (14) and ZC-423 comprises any one of the steps described above, and disclosed in WO 2006/111759 and WO 00/012508.

Preferred Synthesis of ZC-423

In one aspect of the invention there is provided a process of preparing ZC-423 comprising one or more of the steps described above. In a preferred embodiment, the preparation of ZC-423 comprises two or more of the steps described above.

ZC-423 may be prepared in a multi-step synthesis. The intermediates in the synthesis may be one or more of the compounds discussed above.

In a preferred process of preparing ZC-423, the process comprises one or more of the following methods:

(i) the synthesis of compound (11) by oxidation of compound (10) as described herein;

(ii) the synthesis of compound (12) by reaction of compound (11) as described herein;

(iii) the synthesis of compound (13) by reacting compound (12) with methoxyphenylboronic acid as described herein; and (iv) the synthesis of ZC-423 by reacting compound (14) with a bisulphite salt as described herein.

In step (iv), ZC-423 may be prepared by treating compound (14) with a mixture comprising an aqueous solution of a bisulphite salt and an organic solvent that is miscible with the aqueous portion. Alternatively, ZC-423 may be prepared by treating compound (14) with a biphasic mixture comprising an aqueous solution of a bisulphite salt and an organic solvent that is immiscible with the aqueous portion.

Where the steps (i) to (iv) are used in combination in the preparation of ZC-423, the overall yield from compound (10) to the product ZC-423 is significantly increased compared to preparations previously described in the literature.

In one embodiment, the process of preparing ZC-423 may comprise one or more of the steps (i) to (iv) discussed above, and additionally one or more of the following steps:

(v) the synthesis of compound (5) from compound (2) as described herein;

(vi) the synthesis of compound (6) by coupling compound (5) with methyl-4-hydroxypyrrolidine-2-carboxylate as described herein;

(vii) the synthesis of compound (7) by cyclising compound (6) as described herein;

(vii) the synthesis of compound (8) by protecting the hydroxy groups of compound (7) with TBS as described herein;

(viii) the synthesis of compound (9) by protecting the amide nitrogen atoms of compound (8) with SEM as described herein; and (ix) the synthesis of compound (10) by removing the hydroxy-protecting groups of compound (9) as described herein.

In one embodiment, ZC-423 may be prepared from compound (5) via each of the compounds of formula (6) to (14) inclusive. Preferably the synthesis involves each of the steps (i) to (ix) mentioned above. Compared to the synthesis previously disclosed in WO 2006/111759 from compound (5), this route involves fewer chemical transformations. Furthermore, this route reduces the combined total reaction time from compound (5) to ZC-423.

Where the compound of ZC-423 is prepared from compound (5), one or more steps in the synthesis may utilise the most preferred conditions described herein. The use of the most preferred reaction conditions allows ZC-423 to be prepared in higher yield compared to the overall yield for the route disclosed in WO 2006/111759.

Strategies for the Preparation of the Benzodiazepine Ring

WO 2006/111759 describes the preparation of a benzodiazepine ring in a dimer structure. The initial preparation of the ring starts from compound (5) which is coupled with compound (15) to give compound (16).

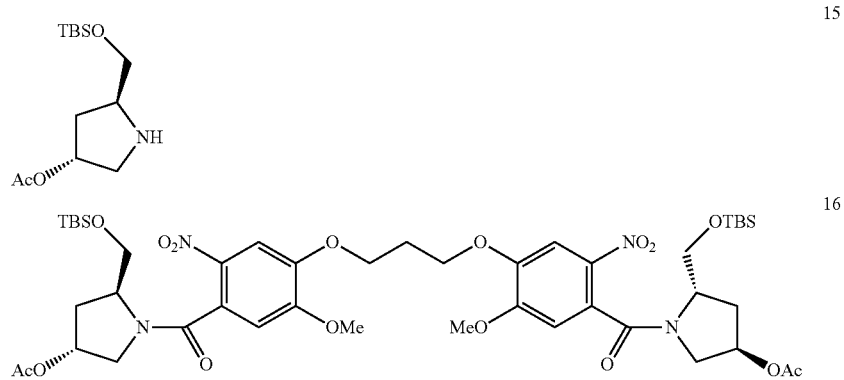

15

16

The nitro group of compound (16) is then reduced to give compound (17).

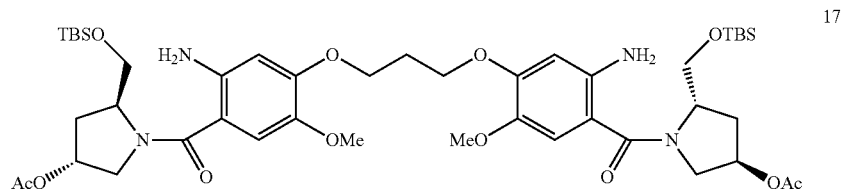 [SMILES: COc1cc(C(=O)N2C[C@H](OC(C)=O)C[C@H]2CO[Si](C)(C)C(C)(C)C)c(N)cc1OCCCOc1cc(N)c(C(=O)N2C[C@H](OC(C)=O)C[C@H]2CO[Si](C)(C)C(C)(C)C)cc1OC]

17

Compound (17) is then treated to remove the silyl protecting groups, to give compound (18).

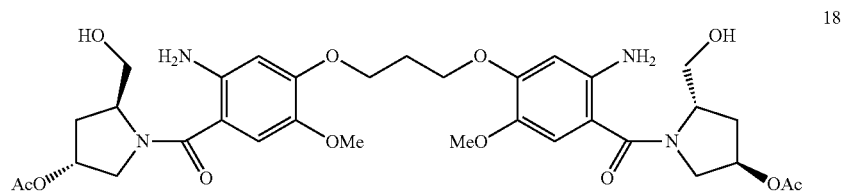 [SMILES: COc1cc(C(=O)N2C[C@H](OC(C)=O)C[C@H]2CO)c(N)cc1OCCCOc1cc(N)c(C(=O)N2C[C@H](OC(C)=O)C[C@H]2CO)cc1OC]

18

Compound (18) is then converted to the benzodiazepine dimer compound of formula (19) by treatment with TEMPO and BAIB (bisacetoxyiodobenzene).

Thus, the preferred method described herein allows the benzodiazepine-containing compound of formula (7) to be prepared from compound (5) in two steps and 79% overall yield. In contrast, the first benzodiazepine-containing compound described in WO 2006/111759 is compound (19) which is obtained from compound (5) in five steps and 15% overall yield.

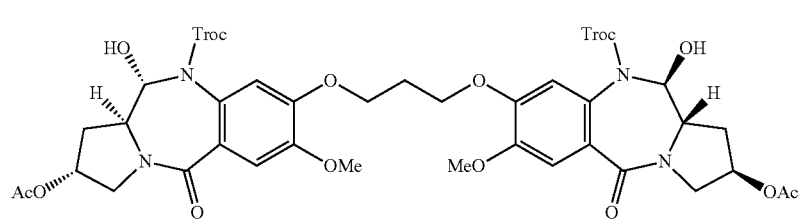

19

Compound (19) is used to prepare compound (20) described in relation to compound (13) above.

The inventors have established that the a dimer comprising a pair of benzodiazepine rings may be prepared from compound (5) in greater yield and in fewer steps compared to the method described in WO 2006/111759.

Abbreviations

The following abbreviations are used in the specification:
DCM dicholromethane
DMF N,N-dimethylformamide
DMSO dimethylsulfoxide
IPA iso-propyl alcohol
SEM 2-(trimethylsilyl)ethoxymethyl
TBAF tetrabutylammonium fluoride TBS tert-butyldimethylsilyl
TCCA trichloroisocyanuric acid
TEMPO 2,2,6,6-tetramethylpiperidine-1-oxyl
TEA triethylamine
Tf triflate; trifluoromethanesulfonyl
TLC thin layer chromatography
TROC 2,2,2-trichloroethoxycarbonyl Experimental Details General Information Reaction progress was monitored by thin-layer chromatography (TLC) using Merck Kieselgel 60 F254 silica gel, with fluorescent indicator on aluminium plates. Visualisation of TLC was achieved with UV light or iodine vapour unless otherwise stated. Flash chromatography was performed using Merck Kieselgel 60 F254 silica gel. Extraction and chromatography solvents were bought and used without further purification from Fisher Scientific, U.K. All chemicals were purchased from Aldrich, Lancaster or BDH.

$^1$H and $^{13}$C NMR spectra were obtained on a Bruker Avance 400 spectrometer. Coupling constants are quoted in hertz (Hz). Chemical shifts are recorded in parts per million (ppm) downfield from tetramethylsilane. Spin multiplicities are described as s (singlet), bs (broad singlet), d (doublet), t (triplet), q (quartet), p (pentuplet) and m (multiplet). IR spectra were recorded on a Perkin-Elmer FT/IR paragon 1000 spectrophotometer by application of the sample in a solution of chloroform using the ATR "golden gate" system. Optical Rotations were measured at ambient temperature using a Bellingham and Stanley ADP 220 polarimeter. Mass spectrometry was performed on a ThermoQuest Navigator from Thermo Electron, Electrospray (ES) spectra were obtained at 20 to 30 V. Accurate mass measurements were performed using Micromass Q-TOF global tandem. All samples were run under electrospray ionization mode using 50% acetonitrile in water and 0.1% formic acid as a solvent. Samples were run on W mode which gives a typical resolution of 19000 at FWHH. The instrument was calibrated with [Glu]-Fibrinopeptide B immediately prior to measurement.

The LC/MS conditions were as follows: The HPLC (Waters Alliance 2695) was run using a mobile phase of water (A) (formic acid 0.1%) and acetonitrile (B) (formic acid 0.1%). Gradient: initial composition 5% B over 1.0 min then 5% B to 95% B within 3 min. The composition was held for 0.5 min at 95% B, and then returned to 5% B in 0.3 minutes. Total gradient run time equals 5 min. Flow rate 3.0 mUmin, 400 µL was split via a zero dead volume tee piece which passes into the mass spectrometer. Wavelength detection range: 220 to 400 nm. Function type: diode array (535 scans). Column: Phenomenex® Onyx Monolithic C18 50×4.60 mm.

Preparation of Compound (5)

A method for the synthesis of nitro-benzoic acid 5 from compound (2) via the compounds of formula (3) and (4) is disclosed in WO 00/012508 and WO 2006/111759. The preparation is illustrated below in Scheme 1.

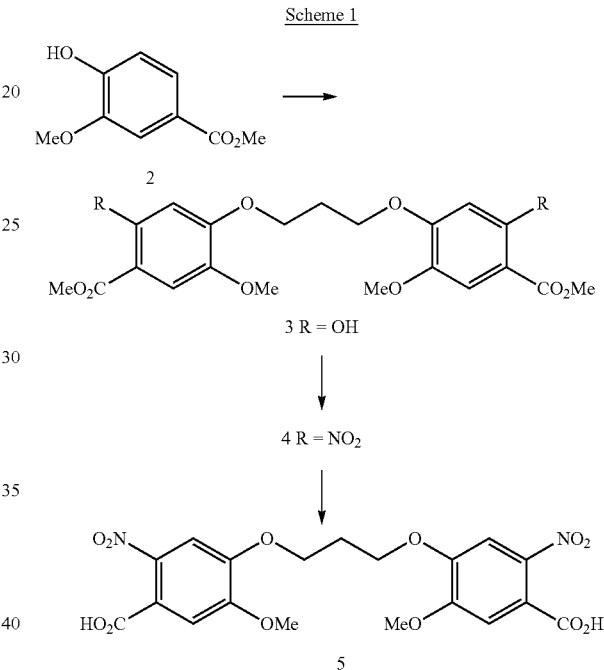

Preparation of Compounds (6) to (14) and ZC-423

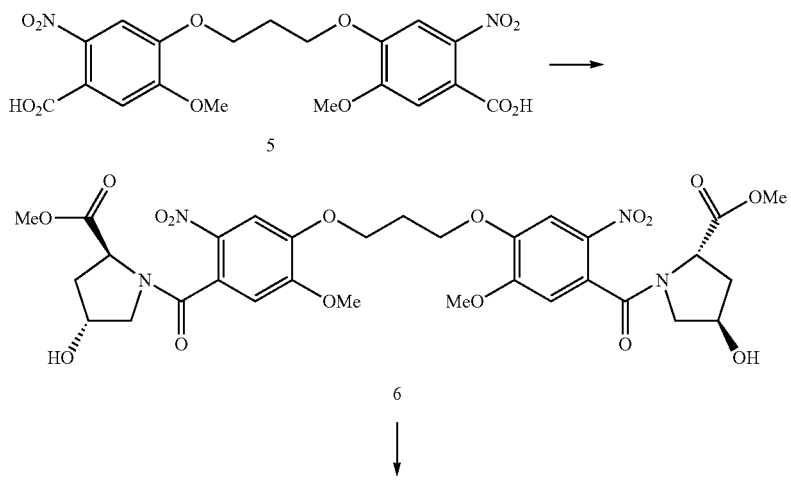

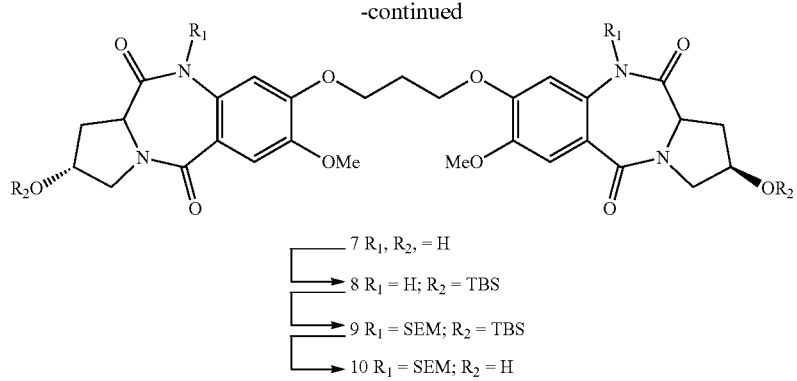

- 7 R₁, R₂, = H
- 8 R₁ = H; R₂ = TBS
- 9 R₁ = SEM; R₂ = TBS
- 10 R₁ = SEM; R₂ = H

Compound (6)

1,1'-[[(Propane-1,3-diyl)dioxy]bis[(5-methoxy-2-nitro-1,4-phenylene)carbonyl]]bis[(2S,4R)-methyl-4-hydroxypyrrolidine-2-carboxylate]

Method A: A catalytic amount of DMF (2 drops) was added (effervescence!) to a stirred solution of the nitro-benzoic acid 5 (1.0 g, 2.15 mmol) and oxalyl chloride (0.95 mL, 1.36 g, 10.7 mmol) in dry THF (20 mL). The reaction mixture was allowed to stir for 16 hours at room temperature and the solvent was removed by evaporation in vacuo. The resulting residue was re-dissolved in dry THF (20 mL) and the acid chloride solution was added dropwise to a stirred mixture of (2S,4R)-methyl-4-hydroxypyrrolidine-2-carboxylate hydrochloride (859 mg, 4.73 mmol) and TEA (6.6 mL, 4.79 g, 47.3 mmol) in THF (10 mL) at −30° C. (dry ice/ethylene glycol) under a nitrogen atmosphere. The reaction mixture was allowed to warm to room temperature and stirred for a further 3 hours after which time TLC (95:5 v/v CHCl₃/MeOH) and LC/MS (2.45 min (ES+) m/z (relative intensity) 721 ([M+H]⁺·, 20)) revealed formation of product. Excess THF was removed by rotary evaporation and the resulting residue was dissolved in DCM (50 mL). The organic layer was washed with 1N HCl (2×15 mL), saturated NaHCO₃ (2×15 mL), H₂O (20 mL), brine (30 mL) and dried (MgSO₄). Filtration and evaporation of the solvent gave the crude product as a dark coloured oil. Purification by flash chromatography (gradient elution: 100% CHCl₃ to 96:4 v/v CHCl₃/MeOH) isolated the pure amide 6 as an orange coloured glass (840 mg, 54%).

Method B: Oxalyl chloride (9.75 mL, 14.2 g, 111 mmol) was added to a stirred suspension of the nitro-benzoic acid 5 (17.3 g, 37.1 mmol) and DMF (2 mL) in anhydrous DCM (200 mL). Following initial effervescence the reaction suspension became a solution and the mixture was allowed to stir at room temperature for 16 hours. Conversion to the acid chloride was confirmed by treating a sample of the reaction mixture with MeOH and the resulting bis-methyl ester was observed by LC/MS. The majority of solvent was removed by evaporation in vacuo, the resulting concentrated solution was re-dissolved in a minimum amount of dry DCM and triturated with diethyl ether. The resulting yellow precipitate was collected by filtration, washed with cold diethyl ether and dried for 1 hour in a vacuum oven at 40° C. The solid acid chloride was added portionwise over a period of 25 minutes to a stirred suspension of (2S,4R)-methyl-4-hydroxypyrrolidine-2-carboxylate hydrochloride (15.2 g, 84.0 mmol) and TEA (25.7 mL, 18.7 g, 185 mmol) in DCM (150 mL) at −40° C. (dry ice/CH₃CN). Immediately, the reaction was complete as judged by LC/MS (2.47 min (ES+) m/z (relative intensity) 721 ([M+H]⁺·, 100)). The mixture was diluted with DCM (150 mL) and washed with 1N HCl (300 mL), saturated NaHCO₃ (300 mL), brine (300 mL), filtered (through a phase separator) and the solvent evaporated in vacuo to give the pure product 6 as an orange solid (21.8 g, 82%).

Analytical Data: $[\alpha]^{22}_D$=−46.1° (c=0.47, CHCl₃); ¹H NMR (400 MHz, CDCl₃) (rotamers) δ 7.63 (s, 2H), 6.82 (s, 2H), 4.79-4.72 (m, 2H), 4.49-4.28 (m, 6H), 3.96 (s, 6H), 3.79 (s, 6H), 3.46-3.38 (m, 2H), 3.02 (d, 2H, J=11.1 Hz), 2.48-2.30 (m, 4H), 2.29-2.04 (m, 4H); ¹³C NMR (100 MHz, CDCl₃) (rotamers) δ 172.4, 166.7, 154.6, 148.4, 137.2, 127.0, 109.7, 108.2, 69.7, 65.1, 57.4, 57.0, 56.7, 52.4, 37.8, 29.0; IR (ATR, CHCl₃) 3410 (br), 3010, 2953, 1741, 1622, 1577, 1519, 1455, 1429, 1334, 1274, 1211, 1177, 1072, 1050, 1008, 871 cm⁻¹; MS (ES⁺) m/z (relative intensity) 721 ([M+H]⁺·, 47), 388 (80); HRMS [M+H]⁺· theoretical $C_{31}H_{36}N_4O_{16}$ m/z 721.2199, found (ES⁺) m/z 721.2227.

Compound (7)

1,1'-[[(Propane-1,3-diyl)dioxy]bis(11aS,2R)-2-(hydroxy)-7-methoxy-1,2,3,10,11,11a-hexahydro-5H-pyrrolo[2,1-c][1,4]-benzodiazepin-5,11-dione]

Method A: A suspension of 10% Pd/C (7.5 g, 10% w/w) in DMF (40 mL) was added to a solution of the nitro-benzoate ester 6 (75 g, 104 mmol) in DMF (360 mL). The suspension was hydrogenated in a Parr hydrogenation apparatus over 8 h. Progress of the reaction was monitored by LC/MS (2.12 min (ES+) m/z (relative intensity) 597 ([M+H]⁺·, 100), (ES−) m/z (relative intensity) 595 ([M+H]⁺·, 100) after the hydrogen uptake had stopped. Solid Pd/C was removed by filtration and the filtrate was concentrated by rotary evaporation under vacuum (below 10 mbar) at 40° C. to afford a dark oil containing traces of DMF and residual charcoal. The residue was digested in EtOH (500 mL) at 40° C. on a water bath (rotary evaporator bath) and the resulting suspension was filtered through celite and washed with ethanol (500 mL) to give a clear filtrate. Hydrazine hydrate (10 mL, 321 mmol) was added to the solution and the reaction mixture was heated at reflux. After 20 minutes the formation of a white precipitate was observed and reflux was allowed to continue for a further 30 minutes. The mixture was allowed to cool down to room temperature and the precipitate was retrieved by filtration, washed with diethyl ether (2*1 volume of precipitate) and dried in a vacuum desiccator to provide 7 (50 g, 81%).

Method B: A solution of the nitro-benzoate ester 6 (6.80 g, 9.44 mmol) in MeOH (300 mL) was added to Raney™ nickel (4 large spatula ends of a ~50% slurry in H₂O) and antibumping granules in a 3-neck round bottomed flask. The mixture was heated at reflux and then treated dropwise with a solution of hydrazine hydrate (5.88 mL, 6.05 g, 188 mmol) in MeOH (50 mL) at which point vigorous effervescence was observed. When the addition was complete (~30 minutes) additional Raney™ nickel was added carefully until effervescence had ceased and the initial yellow colour of the reaction mixture was discharged. The mixture was heated at reflux for a further 30 minutes at which point the reaction was deemed complete by TLC (90:10 v/v $CHCl_3$/MeOH) and LC/MS (2.12 min (ES+) m/z (relative intensity) 597 ([M+H]$^+$·, 100)). The reaction mixture was allowed to cool to around 40° C. and then excess nickel removed by filtration through a sinter funnel without vacuum suction. The filtrate was reduced in volume by evaporation in vacuo at which point a colourless precipitate formed which was collected by filtration and dried in a vacuum desiccator to provide 7 (5.40 g, 96%).

Analytical Data: $[\alpha]^{27}_D$=+404° (c=0.10, DMF); $^1$H NMR (400 MHz, DMSO-$d_6$) δ 10.2 (s, 2H, NH), 7.26 (s, 2H), 6.73 (s, 2H), 5.11 (d, 2H, J=3.98 Hz, OH), 4.32-4.27 (m, 2H), 4.19-4.07 (m, 6H), 3.78 (s, 6H), 3.62 (dd, 2H, J=12.1, 3.60 Hz), 3.43 (dd, 2H, J=12.0, 4.72 Hz), 2.67-2.57 (m, 2H), 2.26 (p, 2H, J=5.90 Hz), 1.99-1.89 (m, 2H); $^{13}$C NMR (100 MHz, DMSO-$d_6$) δ 169.1, 164.0, 149.9, 144.5, 129.8, 117.1, 111.3, 104.5, 54.8, 54.4, 53.1, 33.5, 27.5; IR (ATR, neat) 3438, 1680, 1654, 1610, 1605, 1516, 1490, 1434, 1379, 1263, 1234, 1216, 1177, 1156, 1115, 1089, 1038, 1018, 952, 870 cm$^{-1}$; MS (ES$^+$) m/z (relative intensity) 619 ([M+Na]$^+$·, 10), 597 ([M+H]$^+$·, 52), 445 (12), 326 (11); HRMS [M+H]$^{+\cdot}$ theoretical $C_{29}H_{32}N_4O_{10}$ m/z 597.2191, found (ES$^+$) m/z 597.2205.

Compound (8)

1,1'-[[(Propane-1,3-diyl)dioxy]bis(11aS,2R)-2-(tert-butyldimethylsilyloxy)-7-methoxy-1,2,3,10,11,11a-hexahydro-5H-pyrrolo[2,1-c][1,4]-benzodiazepin-5,11-dione]

TBSCI (317 mg, 2.1 mmol) and imidazole (342 mg, 5.03 mmol) were added to a cloudy solution of the tetralactam 7 (250 mg, 0.42 mmol) in anhydrous DMF (6 mL). The mixture was allowed to stir under a nitrogen atmosphere for 3 h after which time the reaction was deemed complete as judged by LC/MS (3.90 min (ES+) m/z (relative intensity) 825 ([M+H]$^+$·, 100)). The reaction mixture was poured onto ice (~25 mL) and allowed to warm to room temperature with stirring. The resulting white precipitate was collected by vacuum filtration, washed with $H_2O$, diethyl ether and dried in the vacuum desiccator to provide pure 8 (252 mg, 73%).

Analytical Data: $[\alpha]^{23}_D$=+234° (c=0.41, CHCl$_3$); $^1$H NMR (400 MHz, CDCl$_3$) δ 8.65 (s, 2H, NH), 7.44 (s, 2H), 6.54 (s, 2H), 4.50 (p, 2H, J=5.38 Hz), 4.21-4.10 (m, 6H), 3.87 (s, 6H), 3.73-3.63 (m, 4H), 2.85-2.79 (m, 2H), 2.36-2.29 (m, 2H), 2.07-1.99 (m, 2H), 0.86 (s, 18H), 0.08 (s, 12H); $^{13}$C NMR (100 MHz, CDCl$_3$) δ 170.4, 165.7, 151.4, 146.6, 129.7, 118.9, 112.8, 105.3, 69.2, 65.4, 56.3, 55.7, 54.2, 35.2, 28.7, 25.7, 18.0, −4.82 and −4.86; IR (ATR, CHCl$_3$) 3235, 2955, 2926, 2855, 1698, 1695, 1603, 1518, 1491, 1446, 1380, 1356, 1251, 1220, 1120, 1099, 1033 cm$^{-1}$; MS (ES$^+$) m/z (relative intensity) 825 ([M+H]$^+$·, 62), 721 (14), 440 (38); HRMS [M+H]$^+$ theoretical $C_{41}H_{60}N_4O_{10}Si_2$ m/z 825.3921, found (ES$^+$) m/z 825.3948.

Compound (9)

1,1'-[[(Propane-1,3-diyl)dioxy]bis(11aS,2R)-2-(tert-butyldimethylsilyloxy)-7-methoxy-10-((2-(trimethylsilyl)ethoxy)methyl)-1,2,3,10,11,11a-hexahydro-5H-pyrrolo[2,1-c][1,4]-benzodiazepin-5,11-dione]

A solution of n-BuLi (4.17 mL of a 1.6 M solution in hexane, 6.67 mmol) in anhydrous THF (10 mL) was added dropwise to a stirred suspension of the tetralactam 8 (2.20 g, 2.67 mmol) in anhydrous THF (30 mL) at −30° C. (dry ice/ethylene glycol) under a nitrogen atmosphere. The reaction mixture was allowed to stir at this temperature for 1 hour (now a reddish orange colour) at which point a solution of SEMCI (1.18 mL, 1.11 g, 6.67 mmol) in anhydrous THF (10 mL) was added dropwise. The reaction mixture was allowed to slowly warm to room temperature and was stirred for 16 hours under a nitrogen atmosphere. The reaction was deemed complete as judged by TLC (EtOAc) and LC/MS (4.77 min (ES+) m/z (relative intensity) 1085 ([M+H]$^+$·, 100)). The THF was removed by evaporation in vacuo and the resulting residue dissolved in EtOAc (60 mL), washed with $H_2O$ (20 mL), brine (20 mL), dried (MgSO$_4$) filtered and evaporated in vacuo to provide the crude product. Purification by flash chromatography (80:20 v/v Hexane/EtOAc) gave the pure N10-SEM-protected tetralactam 9 as an oil (2.37 g, 82%).

Analytical Data: $[\alpha]^{23}_D$=+163° (c=0.41, CHCl$_3$); $^1$H NMR (400 MHz, CDCl$_3$) δ 7.33 (s, 2H), 7.22 (s, 2H), 5.47 (d, 2H, J=9.98 Hz), 4.68 (d, 2H, J=9.99 Hz), 4.57 (p, 2H, J=5.77 Hz), 4.29-4.19 (m, 6H), 3.89 (s, 6H), 3.79-3.51 (m, 8H), 2.87-2.81 (m, 2H), 2.41 (p, 2H, J=5.81 Hz), 2.03-1.90 (m, 2H), 1.02-0.81 (m, 22H), 0.09 (s, 12H), 0.01 (s, 18H); $^{13}$C NMR (100 MHz, CDCl$_3$) δ 170.0, 165.7, 151.2, 147.5, 133.8, 121.8, 111.6, 106.9, 78.1, 69.6, 67.1, 65.5, 56.6, 56.3, 53.7, 35.6, 30.0, 25.8, 18.4, 18.1, −1.24, −4.73; IR (ATR, CHCl$_3$) 2951, 1685, 1640, 1606, 1517, 1462, 1433, 1360, 1247, 1127, 1065 cm$^{-1}$; MS (ES$^+$) m/z (relative intensity) 1113 ([M+Na]$^+$·, 48), 1085 ([M+H]$^+$·, 100), 1009 (5), 813 (6); HRMS [M+H]$^{+\cdot}$ theoretical $C_{53}H_{88}N_4O_{12}Si_4$ m/z 1085.5548, found (ES$^+$) m/z 1085.5542.

Compound (10)

1,1'-[[(Propane-1,3-diyl)dioxy]bis(11aS,2R)-2-hydroxy-7-methoxy-10-((2-(trimethylsilyl)ethoxy)methyl)-1,2,3,10,11,11a-hexahydro-5H-pyrrolo[2,1-c][1,4]-benzodiazepin-5,11-dione]

A solution of TBAF (5.24 mL of a 1.0 M solution in THF, 5.24 mmol) was added to a stirred solution of the bis-silyl ether 9 (2.58 g, 2.38 mmol) in THF (40 mL) at room temperature. After stirring for 3.5 hours, analysis of the reaction mixture by TLC (95:5 v/v CHCl$_3$/MeOH) revealed completion of reaction. The reaction mixture was poured into a solution of saturated NH$_4$Cl (100 mL) and extracted with EtOAc (3×30 mL). The combined organic layers were washed with brine (60 mL), dried (MgSO$_4$), filtered and evaporated in vacuo to provide the crude product. Purification by flash chromatography (gradient elution: 100% CHCl$_3$ to 96:4 v/v CHCl$_3$/MeOH) gave the pure tetralactam 10 as a white foam (1.78 g, 87%).

Analytical Data: LC/MS 3.33 min (ES+) m/z (relative intensity) 879 ([M+Na]$^+$·, 100), 857 ([M+H]$^+$·, 40); $[\alpha]^{23}_D$=+202° (c=0.34, CHCl$_3$); $^1$H NMR (400 MHz, CDCl$_3$) δ 7.28 (s, 2H), 7.20 (s, 2H), 5.44 (d, 2H, J=10.0 Hz), 4.72 (d, 2H, J=10.0 Hz) 4.61-4.58 (m, 2H), 4.25 (t, 4H, J=5.83 Hz), 4.20-4.16 (m, 2H), 3.91-3.85 (m, 8H), 3.77-3.54 (m, 6H), 3.01 (br s, 2H, OH), 2.96-2.90 (m, 2H), 2.38 (p, 2H, J=5.77 Hz), 2.11-2.05 (m, 2H), 1.00-0.91 (m, 4H), 0.00 (s, 18H); $^{13}$C NMR (100 MHz, CDCl$_3$) δ 169.5, 165.9, 151.3, 147.4, 133.7, 121.5, 111.6, 106.9, 79.4, 69.3, 67.2, 65.2, 56.5, 56.2, 54.1, 35.2, 29.1, 18.4, −1.23; IR (ATR, CHCl$_3$) 2956, 1684, 1625, 1604, 1518, 1464, 1434, 1361, 1238, 1058, 1021 cm$^{-1}$; MS (ES$^+$) m/z (relative intensity) 885 ([M+29]$^{+\cdot}$, 70), 857 ([M+H$^{+\cdot}$, 100), 711 (8), 448 (17); HRMS [M+H]$^{+\cdot}$ theoretical C$_{41}$H$_{60}$N$_4$O$_{12}$Si$_2$ m/z 857.3819, found (ES$^+$) m/z 857.3826.

Compound (11)

1,1'-[[(Propane-1,3-diyl)dioxy]bis[(11aS)-11-sulpho-7-methoxy-2-oxo-10-((2-(trimethylsilyl)ethoxy)methyl)1,2,3,10,11,11a-hexahydro-5H-pyrrolo[2,1-c][1,4]benzodiazepin-5,11-dione]]

Method A: A 0.37 M sodium hypochlorite solution (142.5 mL, 52.71 mmol, 2.4 eq) was added dropwise to a vigorously stirred mixture of the diol 10 (18.8 g, 21.96 mmol, 1 eq), TEMPO (0.069 g, 0.44 mmol, 0.02 eq) and 0.5 M potassium bromide solution (8.9 mL, 4.4 mmol, 0.2 eq) in DCM (115

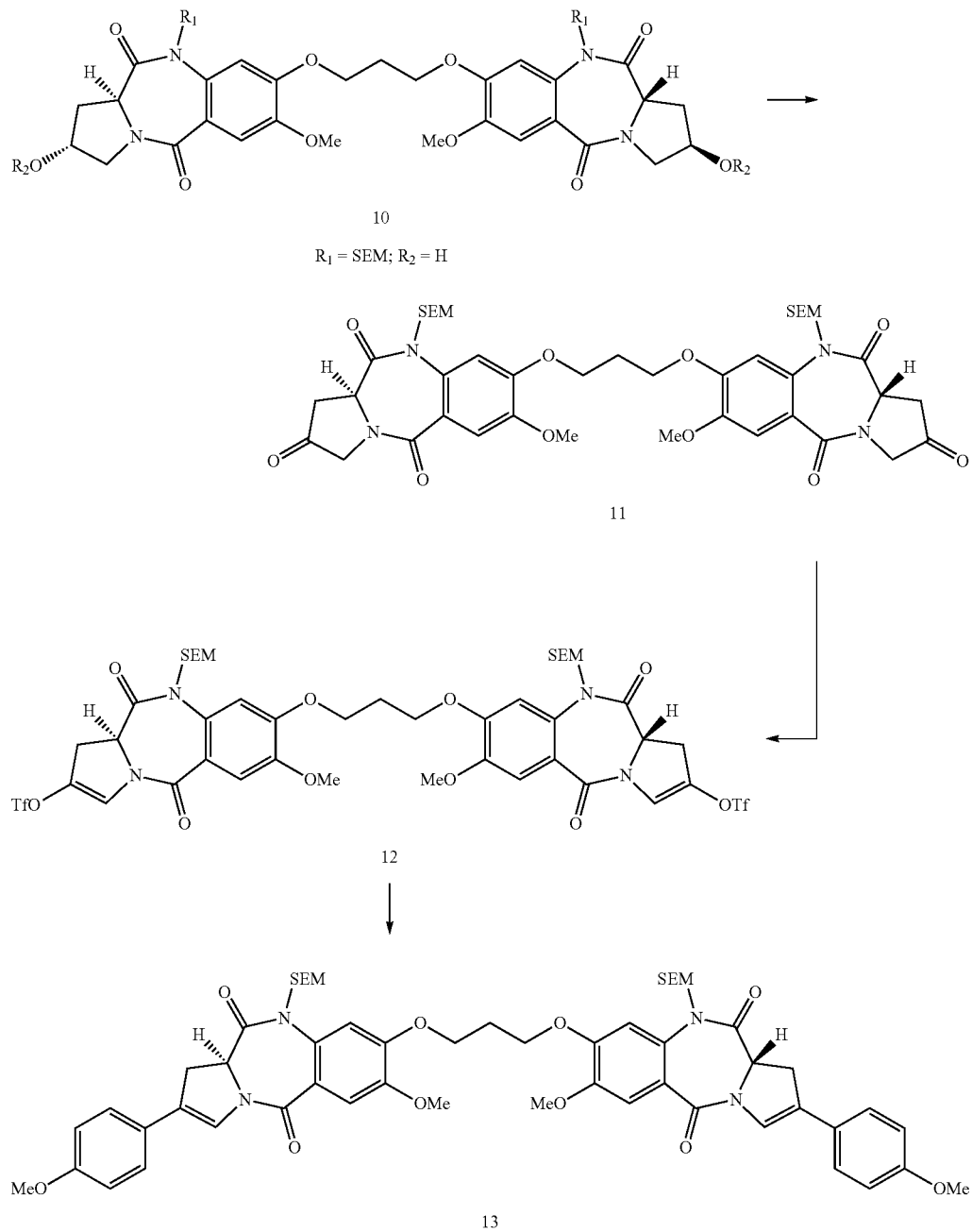

Scheme 3-Preparation of Compounds 11 to 13 mL) at 0° C. The temperature was maintained between 0° C. and 5° C. by adjusting the rate of addition. The resultant yellow emulsion was stirred at 0° C. to 5° C. for 1 hour. TLC (EtOAc) and LC/MS [3.53 min. (ES+) m/z (relative intensity) 875 ([M+Na]$^+$, 50), (ES−) m/z (relative intensity) 852 ([M−H]$^-$, 100)] indicated that reaction was complete.

The reaction mixture was filtered, the organic layer separated and the aqueous layer was backwashed with DCM (×2). The combined organic portions were washed with brine (×1), dried (MgSO$_4$) and evaporated to give a yellow foam. Purification by flash column chromatography (gradient elution 35/65 v/v n-hexane/EtOAC, 30/70 to 25/75 v/v n-hexane/EtOAC) afforded the bis-ketone 11 as a white foam (14.1 g, 75%).

Sodium hypochlorite solution, reagent grade, available at chlorine 10-13%, was used. This was assumed to be 10% (10 g NaClO in 100 g) and calculated to be 1.34 M in NaClO. A stock solution was prepared from this by diluting it to 0.37 M with water. This gave a solution of approximately pH 14. The pH was adjusted to 9.3 to 9.4 by the addition of solid NaHCO$_3$. An aliquot of this stock was then used so as to give 2.4 mol eq. for the reaction.

On addition of the bleach solution an initial increase in temperature was observed. The rate of addition was controlled, to maintain the temperature between 0° C. to 5° C. The reaction mixture formed a thick, lemon yellow coloured, emulsion.

The oxidation was an adaptation of the procedure described in Thomas Fey et al, *J. Org. Chem.*, 2001, 66, 8154-8159.

Method B: Solid TCCA (10.6 g, 45.6 mmol) was added portionwise to a stirred solution of the alcohol 10 (18.05 g, 21.1 mmol) and TEMPO (123 mg, 0.78 mmol) in anhydrous DCM (700 mL) at 0° C. (ice/acetone). The reaction mixture was stirred at 0° C. under a nitrogen atmosphere for 15 min after which time TLC (EtOAc) and LC/MS [3.57 min (ES+) m/z (relative intensity) 875 ([M+Na]$^+$, 50)] revealed completion of reaction. The reaction mixture was filtered through celite and the filtrate was washed with saturated aqueous NaHCO$_3$ (400 mL), brine (400 mL), dried (MgSO$_4$), filtered and evaporated in vacuo to provide the crude product. Purification by flash column chromatography (80:20 v/v EtOAc/Hexane) afforded the bis-ketone 11 as a foam (11.7 g, 65%).

Method C: A solution of anhydrous DMSO (0.72 mL, 0.84 g, 10.5 mmol) in dry DCM (18 mL) was added dropwise over a period of 25 min to a stirred solution of oxalyl chloride (2.63 mL of a 2.0 M solution in DCM, 5.26 mmol) under a nitrogen atmosphere at −60° C. (liq N$_2$/CHCl$_3$). After stirring at −55° C. for 20 min, a slurry of the substrate 10 (1.5 g, 1.75 mmol) in dry DCM (36 mL) was added dropwise over a period of 30 min to the reaction mixture. After stirring for a further 50 min at −55° C., a solution of TEA (3.42 mL, 2.49 g; 24.6 mmol) in dry DCM (18 mL) was added dropwise over a period of 20 min to the reaction mixture. The stirred reaction mixture was allowed to warm to room temperature (~1.5 h) and then diluted with DCM (50 mL). The organic solution was washed with 1 N HCl (2×25 mL), H$_2$O (30 mL), brine (30 mL) and dried (MgSO$_4$). Filtration and evaporation of the solvent in vacuo afforded the crude product which was purified by flash column chromatography (80:20 v/v EtOAc/Hexane) to afford bis-ketone 11 as a foam (835 mg, 56%)

Analytical Data: LC/MS 3.55 min (ES+) m/z (relative intensity) 875 ([M+Na]$^+$, 50); [α]$^{20}_D$=+291° (c=0.26, CHCl$_3$); $^1$H NMR (400 MHz, CDCl$_3$) δ 7.25 (s, 2H), 5.50 (d, 2H, J=10.1 Hz), 4.75 (d, 2H, J=10.1 Hz), 4.60 (dd, 2H, J=9.85, 3.07 Hz), 4.31-4.18 (m, 6H), 3.89-3.84 (m, 8H), 3.78-3.62 (m, 4H), 3.55 (dd, 2H, J=19.2, 2.85 Hz), 2.76 (dd, 2H, J=19.2, 9.90 Hz), 2.42 (p, 2H, J=5.77 Hz), 0.98-0.91 (m, 4H), 0.00 (s, 18H); $^{13}$C NMR (100 MHz, CDCl$_3$) δ 206.8, 168.8, 165.9, 151.8, 148.0, 133.9, 120.9, 111.6, 107.2, 78.2, 67.3, 65.6, 56.3, 54.9, 52.4, 37.4, 29.0, 18.4, −1.24; IR (ATR, CHCl$_3$) 2957, 1763, 1685, 1644, 1606, 1516, 1457, 1434, 1360, 1247, 1209, 1098, 1066, 1023 cm$^{-1}$; MS (ES$^+$) m/z (relative intensity) 881 ([M+29]$^+$, 38), 853 ([M+H]$^+$, 100), 707 (8), 542 (12); HRMS [M+H]$^+$ theoretical C$_{41}$H$_{56}$N$_4$O$_{12}$Si$_2$ m/z 853.3506, found (ES$^+$) m/z 853.3502.

Compound (12)

1,1'-[[(Propane-1,3-diyl)dioxy]bis(11aS)-7-methoxy-2-[[(trifluoromethyl)sulfonyl]oxy]-10-((2-(trimethylsilyl)ethoxy)methyl)-1,10,11,11a-tetrahydro-5H-pyrrolo[2,1-c][1,4]-benzodiazepin-5,11-dione]

Anhydrous 2,6-lutidine (5.15 mL, 4.74 g, 44.2 mmol) was injected in one portion to a vigorously stirred solution of bis-ketone 11 (6.08 g, 7.1 mmol) in dry DCM (180 mL) at −45° C. (dry ice/acetonitrile cooling bath) under a nitrogen atmosphere. Anhydrous triflic anhydride, taken from a freshly opened ampoule (7.2 mL, 12.08 g, 42.8 mmol), was injected rapidly dropwise, while maintaining the temperature at −40° C. or below. The reaction mixture was allowed to stir at −45° C. for 1 h at which point TLC (50/50 v/v n-hexane/EtOAc) revealed the complete consumption of starting material. The cold reaction mixture was immediately diluted with DCM (200 mL) and, with vigorous shaking, washed with water (1×100 mL), 5% citric acid solution (1×200 mL) saturated NaHCO$_3$ (200 mL), brine (100 mL) and dried (MgSO$_4$). Filtration and evaporation of the solvent in vacuo afforded the crude product which was purified by flash column chromatography (gradient elution: 90:10 v/v n-hexane/EtOAc to 70:30 v/v n-hexane/EtOAc) to afford bis-enol triflate 12 as a yellow foam (5.5 g, 70%).

Analytical Data: LC/MS 4.32 min (ES+) m/z (relative intensity) 1139 ([M+Na]$^+$, 20); [α]$^{24}_D$=+271° (c=0.18, CHCl$_3$); $^1$H NMR (400 MHz, CDCl$_3$) δ 7.33 (s, 2H), 7.25 (s, 2H), 7.14 (t, 2H, J=1.97 Hz), 5.51 (d, 2H, J=10.1 Hz), 4.76 (d, 2H, J=10.1 Hz), 4.62 (dd, 2H, J=11.0, 3.69 Hz), 4.32-4.23 (m, 4H), 3.94-3.90 (m, 8H), 3.81-3.64 (m, 4H), 3.16 (ddd, 2H, J=16.3, 11.0, 2.36 Hz), 2.43 (p, 2H, J=5.85 Hz), 1.23-0.92 (m, 4H), 0.02 (s, 18H); $^{13}$C NMR (100 MHz, CDCl$_3$) δ 167.1, 162.7, 151.9, 148.0, 138.4, 133.6, 120.2, 118.8, 111.9, 107.4, 78.6, 67.5, 65.6, 56.7, 56.3, 30.8, 29.0, 18.4, −1.25; IR (ATR, CHCl$_3$) 2958, 1690, 1646, 1605, 1517, 1456, 1428, 1360, 1327, 1207, 1136, 1096, 1060, 1022, 938, 913 cm$^{-1}$; MS (ES$^+$) m/z (relative intensity) 1144 ([M+28]$^+$, 100), 1117 ([M+H]$^+$, 48), 1041 (40), 578 (8); HRMS [M+H]$^+$ theoretical C$_{43}$H$_{54}$N$_4$O$_{16}$Si$_2$S$_2$F$_6$ m/z 1117.2491, found (ES$^+$) m/z 1117.2465.

Compound (13)

1,1'-[[(Propane-1,3-diyl)dioxy]bis(11aS)-7-methoxy-2-(p-methoxyphenyl)-10-((2-(trimethylsilyl)ethoxy)methyl)-1,10,11,11a-tetrahydro-5H-pyrrolo[2,1-c][1,4]-benzodiazepin-5,11-dione]

Pd[PPh$_3$]$_4$ (510 mg, 440 μmol) was added to a stirred mixture of the bis-enol triflate 12 (12.35 g, 11.1 mmol), 4-methoxyphenylboronic acid (4.35 g, 28.6 mmol), Na$_2$CO$_3$ (3.76 g, 35.5 mmol), EtOH (61 mL), toluene (122 mL) and water (61 mL). The reaction mixture was allowed to stir under a nitrogen atmosphere for 3 hours after which time the complete consumption of starting material was observed by TLC (EtOAc) and LC/MS (4.20 min (ES+) m/z (relative intensity) 1034 ([M+2H]⁺·, 100)). The reaction mixture was diluted with EtOAc (400 mL) and washed with H₂O (2×300 mL), brine (200 mL), dried (MgSO₄), filtered and evaporated under reduced pressure to provide the crude product. Purification by flash chromatography (gradient elution: 80:20 v/v Hexane/EtOAc to 60:40 v/v Hexane/EtOAc) afforded bis-C2-aryl compound 13 as a yellowish foam (10.0 g, 87%):

Analytical Data: [α]²⁴_D=+328° (c=0.16, CHCl₃); ¹H NMR (400 MHz, CDCl₃) δ 7.39 (s, 2H), 7.37 (d, 4H, J=8.76 Hz), 7.33-7.32 (m, 2H), 7.28 (s, 2H), 6.88 (d, 4H, J=8.83 Hz), 5.52 (d, 2H, J=10.0 Hz), 4.77 (d, 2H, J=10.0 Hz), 4.61 (dd, 2H, J=10.6, 3.36 Hz), 4.31-4.26 (m, 4H), 3.96-3.91 (m, 8H), 3.81-3.64 (m, 10H), 3.13 (ddd, 2H, J=16.1, 10.6, 2.13 Hz), 2.45 (p, 2H, J=5.83 Hz), 1.04-0.93 (m, 4H), 0.02 (s, 18H); ¹³C NMR (100 MHz, CDCl₃) δ 168.5, 161.6, 159.3, 151.4, 147.7, 133.6, 126.6, 125.6, 121.7, 120.3, 114.2, 111.8, 107.2, 78.4, 67.2, 65.5, 57.6, 56.3, 55.4, 31.6, 29.0, 18.4, −1.22; IR (ATR, CHCl₃) 2943, 1685, 1637, 1604, 1564, 1556, 1532, 1514, 1456, 1431, 1358, 1246, 1202, 1179, 1134, 1100, 1066 cm⁻¹; MS (ES⁺) m/z (relative intensity) 1061 ([M+29]⁺·, 100), 1033 ([M+H]⁺·, 55), 957 (50), 768 (10), 445 (18); HRMS [M+H]⁺· theoretical C₅₅H₆₈N₄O₁₂Si₂ m/z 1033.4445, found (ES⁺) m/z 1033.4443.

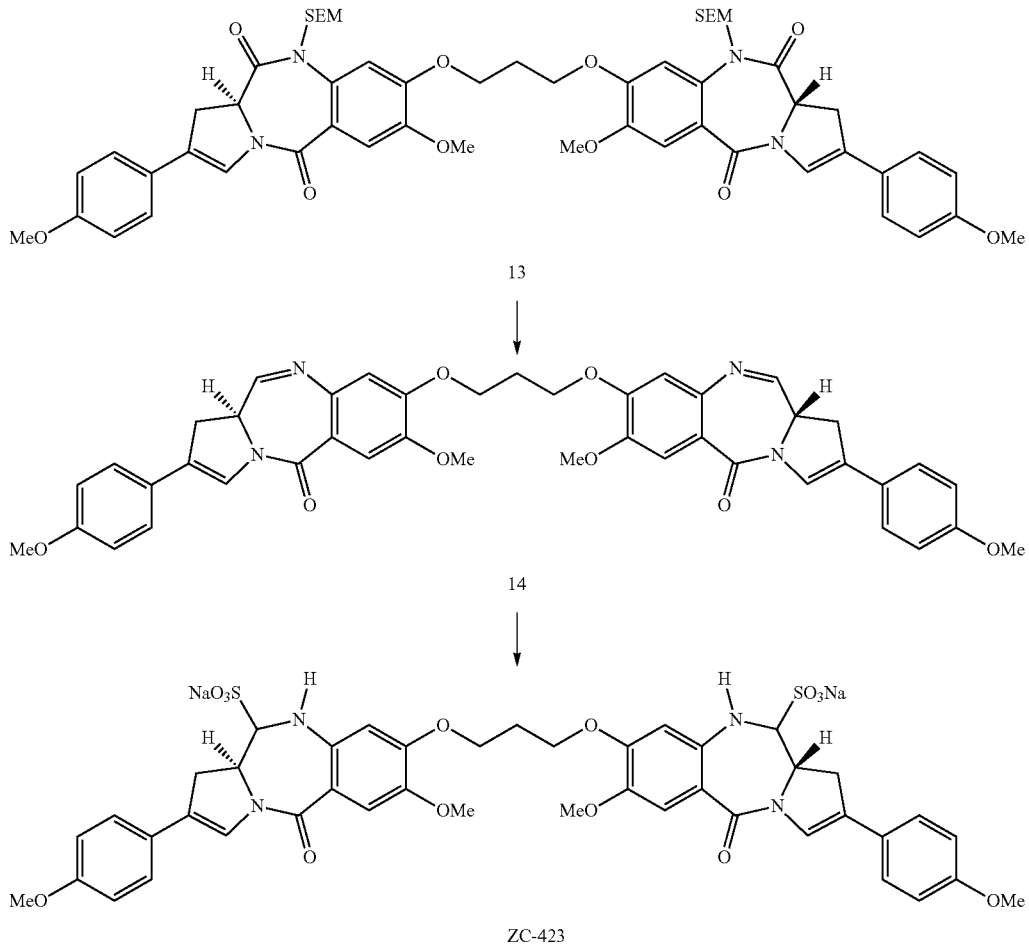

Scheme 4-Preparations of Compounds 14 and ZC-423

Compound (14)

1,1'-[[(Propane-1,3-diyl)dioxy]bis[(11aS)-7-methoxy-2-(p-methoxyphenyl)-1,11a-dihydro-5H-pyrrolo[2,1-c][1,4]benzodiazepine-5-one]] (SG-2202)

Method A: LiBH₄ (857 mg, 39.34 mmol) was added to a stirred solution of the SEM-tetralactam 13 (2.71 g, 2.62 mmol) in THF (100 mL) and EtOH (100 mL). The reaction mixture was allowed to stir under a nitrogen atmosphere for 2 hours after which time the complete conversion of starting material directly to N10/C11-imine was observed by LC/MS (3.02 min (ES+) m/z (relative intensity) 742 ([M+H]⁺·, 100)). The solvent was removed by evaporation in vacuo and the resulting white solid treated with H₂O (650 mL) and extracted with DCM (3×350 mL). The combined organic layers were washed with H₂O (450 mL), brine (450 mL) and evaporated in vacuo to provide the crude SEM-carbinolamine 13b (1.95 g, 72%). A sample of 13b (502 mg, 0.484 mmol) was immediately dissolved in acetonitrile (20 mL, formic acid 0.1%) and H₂O (20 mL, formic acid 0.1%). The reaction mixture was allowed to stir at room temperature for 2 hours after which time the formation of a significant quantity of desired product was observed by TLC (95:5 v/v $CHCl_3$/MeOH). The reaction mixture was diluted with DCM (100 ml) and the organic layer washed with saturated $NaHCO_3$ (50 mL), $H_2O$ (50 mL), brine (50 mL), dried ($MgSO_4$), filtered and evaporated in vacuo to provide the crude product. Purification by flash chromatography (gradient elution: 100% $CHCl_3$ to 98:2 v/v $CHCl_3$/MeOH) gave the pure N10/C11-imine 14 (SG-2202), after repeated cycles of $CHCl_3$ evaporation, as an orange foam (208 mg, 58%).

Method B: $LiBH_4$ (5 g, 229 mmol) was added portionwise to a stirred solution of the SEM-tetralactam 13 (12.4 g, 12 mmol) in THF (120 mL) and EtOH (120 mL). An exotherm accompanied by vigorous foaming was observed and the temperature was maintained between 15° C. and 25° C. with the aid of a cooling bath (ice/water). The reaction mixture was allowed to stir for 1 h after which time the complete conversion of starting material directly was observed by LC/MS {3.02 min (ES+) m/z (relative intensity) 741 ([M+H]$^+$·, 100)}. The reaction mixture was carefully diluted with $H_2O$ (500 mL) and extracted with DCM (1×500 mL, 1×200 mL, 1×100 mL). The combined organic layers were washed with water (1×500 mL), brine (1×200 mL), dried over $MgSO_4$, filtered and evaporated under reduced pressure at 35° C. to provide the intermediate SEM-carbinolamine. The white solid (12.4 g) was immediately dissolved in EtOH (400 mL), DCM (150 mL) and $H_2O$ (50 mL) and treated with flash silica gel (300 g). The thick suspension was allowed to stir at room temperature for 72 h after which time the formation of a significant quantity of desired product was observed by TLC (95:5 v/v $CHCl_3$/MeOH). The reaction mixture was filtered through a wide porosity 3 sinter funnel and the pad rinsed slowly and thoroughly with 90:10 v/v $CHCl_3$/MeOH until no further product eluted (checked by TLC). The filtrate was washed with brine (300 mL), dried ($MgSO_4$), filtered and evaporated in vacuo, followed by high vacuum drying, to provide the crude product. Purification by flash chromatography (gradient elution: 100% HPLC grade $CHCl_3$ to 98:2 v/v $CHCl_3$/MeOH) gave 14 (SG-2202) as a mixture of carbinolamine ethers and imine (8.4 g, 94%). In order to obtain an NMR sample, material (100 mg) was treated with HPLC grade $CHCl_3$ (50 mL) and allowed to stand overnight to promote the formation of the imine form. The solvent was removed by evaporation under reduced pressure, and the residue was again treated with HPLC grade $CHCl_3$ (50 mL) and allowed to strand for 4 h. The process was repeated several times and the final sample analysed by NMR and optical rotation.

Method C: $LiBH_4$ (3.52 g, 161.8 mmol) was added in one portion to a stirred solution of the SEM-tetralactam 13 (8.35 g, 8.1 mmol) in THF (160 mL) and EtOH (160 mL) at −5 to −10° C. (ice/acetone). The cold bath was removed and the reaction mixture was allowed to reach room temperature. The reaction mixture was allowed to stir for 1 h after which time the complete conversion of starting material was observed by LC/MS (2.98 min (ES+) m/z (relative intensity) 741 ([M+H]$^+$·, 100)). The reaction mixture was carefully poured onto a mixture of crushed ice (250 mL) and 0.5 M citric acid solution (250 mL) (vigorous effervescence). The mixture was stirred for 5 min. and DCM (250 mL) was added. The organic portion was separated and the aqueous portion was washed with DCM (2×250 mL). The combined organic layers were washed with 0.5 M citric acid solution (3×250 mL), saturated sodium hydrogen carbonate solution (300 mL), water (300 mL), brine (300 mL), dried over $MgSO_4$, and evaporated in vacuo at 30° C. to give crude 14 (SG-2202). Purification by flash column chromatography ($CHCl_3$ then $CHCl_3$/MeOH: 99.5%/0.5%, 99%/1%, 98.5%/1.5% and 98%/2%) afforded the product 14 (SG-2202) as a yellow foam (4.52 g, 75%). A sample of the product (250 mg) in HPLC grade $CHCl_3$ (25 mL) was stirred at room temperature for 18 h. and the solvent was evaporated in vacuo. The product was again dissolved in HPLC grade $CHCl_3$ (25 mL) and stirred at room temperature for 2 h then evaporated in vacuo. This process was repeated a further two times to give the product 14 (SG-2202) in the imine form for NMR. An analytical sample was recrystallised from EtOAc.

Method D: $NaBH_4$ (77 mg, 2.03 mmol) was added to a stirred solution of the SEM-tetralactam 13 (105 mg, 0.10 mmol) in THF (5 mL) and EtOH (2.5 mL). The reaction mixture was allowed to stir under a nitrogen atmosphere for 20 h after which time the complete conversion of starting material directly to N10/C11-imine was observed by LC/MS (3.02 min (ES+) m/z (relative intensity) 741 ([M+H]$^+$·, 100)). The solvent was removed by evaporation in vacuo and the resulting residue treated with $H_2O$ (30 mL) and extracted with DCM (3×15 mL). The combined organic layers were washed with $H_2O$ (10 mL), brine (20 mL) and evaporated in vacuo to provide the intermediate SEM-carbinolamine. The intermediate may be treated with silica gel as described above in method B.

Analytical Data (for product of Method B): $[\alpha]^{19}_D$=+1061° (c=1, $CHCl_3$) [lit $[\alpha]^{20}_D$=+880° (c=0.22, $CHCl_3$)]; $^1$H NMR (400 MHz, $CDCl_3$) δ 7.87 (d, 2H, J=3.95 Hz), 7.52 (s, 2H), 7.38 (s, 2H), 7.32 (d, 4H, J=8.66 Hz), 6.89 (d, 4H, J=8.74 Hz), 6.87 (s, 2H), 4.40-4.20 (m, 6H), 3.94 (s, 6H), 3.82 (s, 6H), 3.56 (ddd, 2H, J=16.2, 11.6, 1.86 Hz), 3.40-3.35 (m, 2H), 2.46-2.37 (m, 2H) [lit $^1$H NMR (400 MHz, $CDCl_3$) δ 7.79 (d, 2H, J=3.9 Hz), 7.44 (s, 2H), 7.30 (s, 2H), 7.24 (d, 4H, J=8.7 Hz), 6.81 (d, 4H, J=8.7 Hz), 6.79 (s, 2H), 4.30-4.18 (m, 6H), 3.86 (s, 6H), 3.74 (s, 6H), 3.48 (dd, 2H, J=11.8, 16.2 Hz), 2.85 (d, 2H, J=16.2 Hz), 2.38-2.32 (m, 2H)].

Compound ZC-423

1,1'-[[(Propane-1,3-diyl)dioxy]bis[(11aS)-11-sulpho-7-methoxy-2-methoxybenzene-1,10,11,11a-tetrahydro-5H-pyrrolo[2,1-c][1,4]benzodiazepin-5-one]] sodium salt (SG-2285)

Method A: Sodium bisulphite (538 mg, 5.17 mmol) was added to a stirred suspension of 14 (1.82 g, 2.46 mmol) in IPA (364 mL) and water (182 mL). The reaction mixture was allowed to stir vigorously and eventually became clear (~40 minutes). After a total of 45 minutes stirring at room temperature the precipitate was collected by vacuum filtration, rinsed with water (182 mL) and dried to provide an orange solid (208 mg). The identity of the precipitate was later confirmed by LC/MS and $^1$H NMR as pure unreacted compound (14). Without delay, the filtrate (728 mL) was immediately frozen (liquid nitrogen bath at −196° C.) and lyophilised over a period of three days to give a pale yellow foam which was suspended in EtOAc (600 mL) and stirred for 1 hour. The solid was collected in a sinter funnel by vacuum filtration and washed with EtOAc (3×150 mL) to provide the bisulphite adduct ZC-423 as an off white solid (1.91 g, 82%).

The product was obtained as a mixture of diastereoisomers as determined by LC/MS (see FIG. 1) (27.5 S,S: 1 S,R; 96.5% S,S: 3.5% S,R). The minor diastereoisomer could not be distinguished by NMR.

Analytical Data: $^1$H NMR (400 MHz, d$_6$-DMSO) δ 7.43 (s, 2H), 7.39 (d, 4H, J=8.68 Hz), 7.07 (s, 2H), 6.93 (d, 4H, J=8.8 Hz), 6.54 (s, 2H), 5.29 (s, 2H), 4.36-4.28 (m, 2H), 4.20-4.12 (m, 4H), 3.96 (d, 2H, J=10.4 Hz), 3.78 (s, 6H), 3.74 (s, 6H), 3.55-3.47 (m, 2H), 3.30-3.18 (m, 2H), 2.27-2.18 (m, 2H).

Method B: A solution of sodium bisulphite (142 mg, 1.36 mmol, 2.0 equiv.) in H$_2$O (30 mL) was added to a solution of compound (14) (504 mg, 0.68 mmol) in DCM (30 mL). The reaction mixture was allowed to stir vigorously at room temperature for 25 h. HPLC analysis of the aqueous layer revealed formation of ZC-423 and complete absence of the starting material. The reaction mixture was diluted with DCM (100 mL) and H$_2$O (100 mL). The aqueous layer was separated (without shaking the separating funnel) and washed with DCM. The resulting solution was immediately frozen (liquid nitrogen bath) and lyophilised to give a white foam, which was suspended in EtOAc (100 mL) and stirred for 15 min. The solid was collected by filtration to provide the bisulphite adduct ZC-423 as an off white solid (400 mg, 62%).

The product was obtained as a mixture of diastereoisomers (S,R:S,S=9:1), after freeze-drying. FIG. 2 shows the LC/MS trace before freeze-dying (95.8% S,R: 4.2% S,S).

Analytical Data: $^1$H NMR (400 MHz, d$_6$-DMSO) δ 7.44-7.30 (m, 7H), 7.08 (s, 1H), 7.00 (d, 1H, J=5.96 Hz), 6.95-6.90 (m, 4H), 6.54 (s, 2H), 5.28 (s, 1H), 4.46-4.41 (m, 1H), 4.35-4.29 (m, 1H), 4.15-4.08 (m, 5H), 3.96 (d, 1H, J=10.3 Hz), 3.78-3.69 (m, 13H), 3.52-3.49 (m, 1H), 3.29-3.17 (m, 2H), 2.24-2.23 (m, 2H); $^{13}$C NMR (100 MHz, d$_6$-DMSO) δ 163.85, 158.22, 151.29, 143.10, 140.09, 126.77, 126.00, 122.53, 122.15, 115.43, 114.05, 112.73, 106.53, 78.36, 65.07, 56.72, 55.98, 55.10, 35.45, 28.61.

References

The following references are incorporated by reference in their entirety.
WO 00/012508
WO 2004/043963
WO 2005/085251
WO 2006/111759
Japanese Patent 58-180 487
Antonow et al *J. Comb. Chem.*, 2007, 9, 437-445
Arima, et al., *J. Antibiotics*, 25, 437-444 (1972)
Bose, et al., *Tetrahedron*, 48, 751-758 (1992)
Hara, et al., *J. Antibiotics*, 41, 702-704 (1988)
Hochlowski, et al., *J. Antibiotics*, 40, 145-148 (1987)
Hu, et al., *J. Org. Chem.*, 66, 2881-2883 (2001)
Hurley and Needham-VanDevanter, *Acc. Chem. Res.*, 19, 230-237 (1986)
Itoh, et al., *J. Antibiotics*, 41, 1281-1284 (1988)
Kohn, In *Antibiotics III*. Springer-Verlag, New York, pp. 3-11 (1975)
Konishi, et al., *J. Antibiotics*, 37, 200-206 (1984)
Kuminoto, et al., *J. Antibiotics*, 33, 665-667 (1980)
Langley and Thurston, *J. Org. Chem.*, 52, 91-97 (1987)
Leber, et al., *J. Am. Chem. Soc.*, 110, 2992-2993 (1988)
Leimgruber, et al., *J. Am. Chem. Soc.*, 87, 5793-5795 (1965)
Leimgruber, et al., *J. Am. Chem. Soc.*, 87, 5791-5793 (1965)
Shimizu, et al, *J. Antibiotics*, 29, 2492-2503 (1982)
Takeuchi, et al., *J. Antibiotics*, 29, 93-96 (1976)
Thomas Fey et al, *J. Org. Chem.*, 2001, 66, 8154-8159
Thurston et al., *Chem. Brit.*, 26, 767-772 (1990)
Thurston, et al., *Chem. Rev.* 1994, 433-465 (1994)
Tsunakawa, et al., *J. Antibiotics*, 41, 1366-1373 (1988)

The invention claimed is:
1. A method of preparing ZC-423:

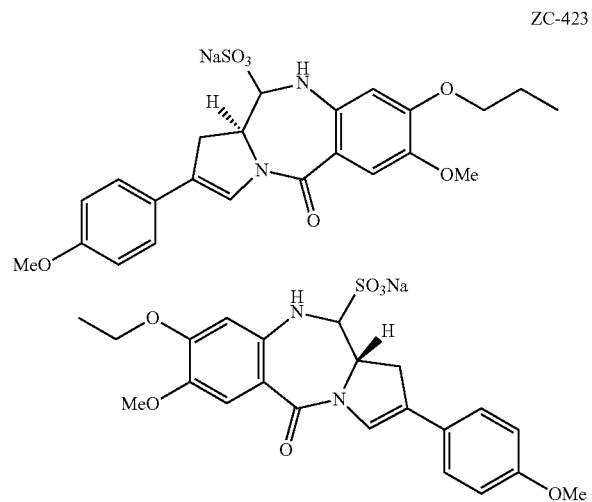

the method comprising the step of treating compound (14):

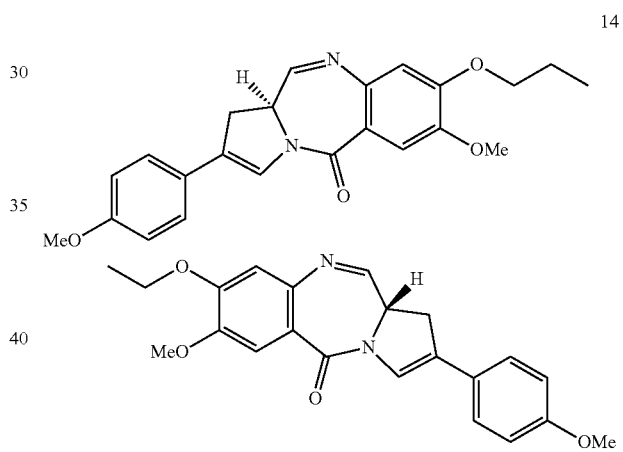

with a biphasic solvent mixture comprising sodium bisulphite, wherein the biphasic solvent mixture comprises an aqueous solution of the bisulphite salt and an organic solvent that is immiscible with the aqueous solution, and compound (14) is treated with the bisulphite salt for 12 hours or more.

2. The method of claim 1, wherein the organic solvent is a solvent that dissolves compound (14).

3. The method of claim 2, wherein the organic solvent is DCM.

4. The method of claim 1, wherein compound (14) is treated with the bisulphite salt for 24 hours or more.

5. The method of claim 1 wherein the product of the reaction is frozen soon after the reaction is deemed complete.

6. The method of claim 5, wherein in the product of the reaction is frozen to a temperature of −100° C. or below.

7. The method of claim 6, wherein in the product of the reaction is frozen to a temperature of −190° C. or below.

8. The method of claim 5 further comprising the step of freeze-drying the product after the product is frozen.

9. Compound ZC-423 comprising 70% or more of the S,R-diastereomer.

10. A method of preparing ZC-423:

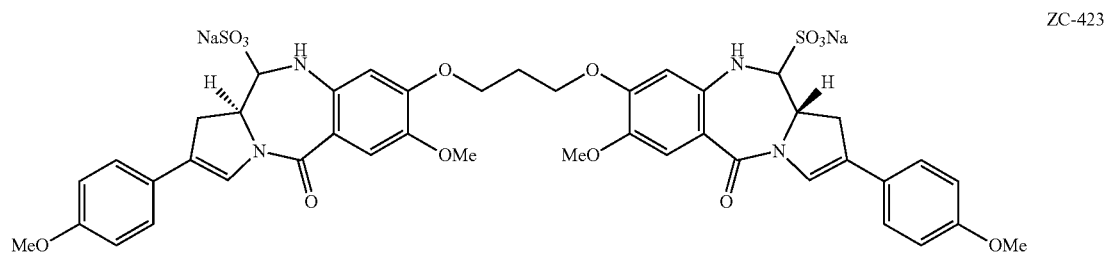

the method comprising the step of treating compound (14)

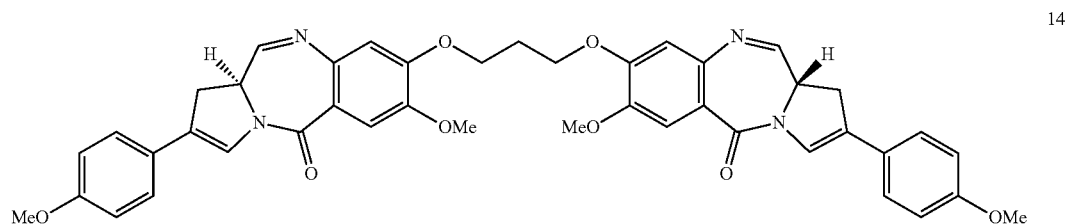 [SMILES: COc1ccc(C2=CN3C(=O)c4cc(OC)c(OCCCOc5cc6c(cc5OC)C(=O)N5C=C(c7ccc(OC)cc7)C[C@H]5C=N6)cc4N=C[C@@H]3C2)cc1]

with a solvent mixture comprising sodium bisulphite, wherein the solvent mixture comprises an aqueous solution of the bisulphite salt and an organic solvent that is miscible with the aqueous solution.

11. The method of claim 10, wherein the organic solvent is an alkyl alcohol.

12. The method of claim 11, wherein the alkyl alcohol is propyl alcohol.

13. The method of claim 11, wherein the propyl alcohol is isopropylalcohol (IPA).

14. The method of claim 10, wherein the product of the reaction is frozen soon after the reaction is deemed complete.

15. The method of claim 14, wherein in the product of the reaction is frozen to a temperature of −100° C. or below.

16. The method of claim 15, wherein in the product of the reaction is frozen to a temperature of −190° C. or below.

17. The method of claim 14 further comprising the step of freeze-drying the product after the product is frozen.

18. Compound ZC-423 comprising 70% or more of the S,S-diastereomer.

* * * * *

UNITED STATES PATENT AND TRADEMARK OFFICE
CERTIFICATE OF CORRECTION

PATENT NO.      : 8,501,934 B2  
APPLICATION NO. : 13/055194  
DATED           : August 6, 2013  
INVENTOR(S)     : Howard et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 362 days.

Signed and Sealed this
Twenty-sixth Day of November, 2013

Margaret A. Focarino
*Commissioner for Patents of the United States Patent and Trademark Office*

UNITED STATES PATENT AND TRADEMARK OFFICE
CERTIFICATE OF CORRECTION

PATENT NO. : 8,501,934 B2  
APPLICATION NO. : 13/055194  
DATED : August 6, 2013  
INVENTOR(S) : Howard et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 360 days.

Signed and Sealed this

Fifteenth Day of September, 2015

Michelle K. Lee
*Director of the United States Patent and Trademark Office*